United States Patent
Nunomura et al.

(10) Patent No.: US 7,549,429 B2
(45) Date of Patent: Jun. 23, 2009

(54) ULTRASONIC WASHING DEVICE

(75) Inventors: Mahito Nunomura, Hirakata (JP); Takashi Kishimoto, Kobe (JP)

(73) Assignee: Panasonic Electric Works Co., Ltd., Osaka (JP)

(*) Notice: Subject to any disclaimer, the term of this patent is extended or adjusted under 35 U.S.C. 154(b) by 565 days.

(21) Appl. No.: 10/546,876

(22) PCT Filed: Feb. 25, 2004

(86) PCT No.: PCT/JP2004/002234
§ 371 (c)(1),
(2), (4) Date: Jan. 24, 2006

(87) PCT Pub. No.: WO2004/075706
PCT Pub. Date: Sep. 10, 2004

(65) Prior Publication Data
US 2006/0191562 A1   Aug. 31, 2006

(30) Foreign Application Priority Data
Feb. 25, 2003   (JP)   ............... 2003-048024
Sep. 30, 2003   (JP)   ............... 2003-342586

(51) Int. Cl.
*B08B 3/10* (2006.01)
(52) U.S. Cl. .................... 134/184; 134/198
(58) Field of Classification Search ............ 68/3 SS; 134/184, 186
See application file for complete search history.

(56) References Cited

U.S. PATENT DOCUMENTS 2,949,900 A * 8/1960 Bodine .................. 123/472
2,980,123 A * 4/1961 Lemelson .................. 134/184
3,154,890 A * 11/1964 Lemelson .................. 451/165
3,168,659 A * 2/1965 Bayre et al. ................ 310/337
3,373,752 A * 3/1968 Kiyoshi ........................ 134/1

(Continued)

FOREIGN PATENT DOCUMENTS

JP   51-53766   5/1976

(Continued)

OTHER PUBLICATIONS

English language Abstract of JP6-218337.

(Continued)

*Primary Examiner*—Frankie L Stinson
(74) *Attorney, Agent, or Firm*—Greenblum & Bernstein, P.L.C.

(57) ABSTRACT

In an ultrasonic washer for washing by splaying washing toward an object to be washed or a portion to be washed from a front end of a nozzle, a part of an ultrasonic wave propagation member connected to an ultrasonic transducer is protruded into a cavity of the nozzle into which the washing is filled in order to propagate ultrasonic vibration generated by the ultrasonic transducer to the washing efficiently. Furthermore, the ultrasonic wave propagation member is formed so that a cross-sectional area becomes gradually smaller as approaching to the front end thereof, so that the ultrasonic vibration is converged to the end face of the ultrasonic wave propagation member. Still furthermore, a length of the ultrasonic transducer and the ultrasonic wave propagation member is made to be integral multiplication of a half-wavelength of ultrasonic standing wave oscillation, and the end face of the ultrasonic wave propagation member from which the ultrasonic wave is emitted to the washing is disposed at a position of antinode of the ultrasonic standing wave oscillation where the amplitude becomes the largest.

17 Claims, 28 Drawing Sheets

U.S. PATENT DOCUMENTS

| | | | |
|---|---|---|---|
| 4,326,553 A * | 4/1982 | Hall | 134/153 |
| 4,537,511 A | 8/1985 | Frei | |
| 4,646,967 A * | 3/1987 | Geithman | 239/4 |
| 5,100,476 A * | 3/1992 | Mase et al. | 134/1 |
| 5,312,281 A | 5/1994 | Takahashi et al. | |
| 5,927,306 A * | 7/1999 | Izumi et al. | 134/155 |
| 5,975,098 A * | 11/1999 | Yoshitani et al. | 134/148 |
| 6,003,527 A * | 12/1999 | Netsu et al. | 134/1.3 |
| 6,189,547 B1 * | 2/2001 | Miyamoto et al. | 134/57 R |
| 6,343,609 B1 * | 2/2002 | Kim | 134/1.3 |
| 6,729,339 B1 * | 5/2004 | Boyd et al. | 134/184 |
| 2001/0037537 A1 | 11/2001 | Kitaori et al. | |

FOREIGN PATENT DOCUMENTS

| | | | |
|---|---|---|---|
| JP | 63-016943 | * | 1/1988 |
| JP | 64-39890 | | 3/1989 |
| JP | 5-43437 | | 7/1993 |
| JP | 5-277413 | | 10/1993 |
| JP | 6-218337 | | 8/1994 |
| JP | 9-122612 | | 5/1997 |
| JP | 9-141220 | | 6/1997 |
| JP | 11-047061 | * | 2/1999 |
| JP | 2000-246199 | | 9/2000 |
| JP | 2001-310094 | | 11/2001 |
| JP | 2002-66477 | | 3/2002 |

OTHER PUBLICATIONS

English language Abstract of JP 2001-310094.
English language Abstract of JP 2002-66477.
English language Abstract of JP 9-141220.
English language Abstract of JP 2000-246199.
English language Abstract of JP 9-122612.
English language Abstract of JP 5-277413.

* cited by examiner

FIG. 5
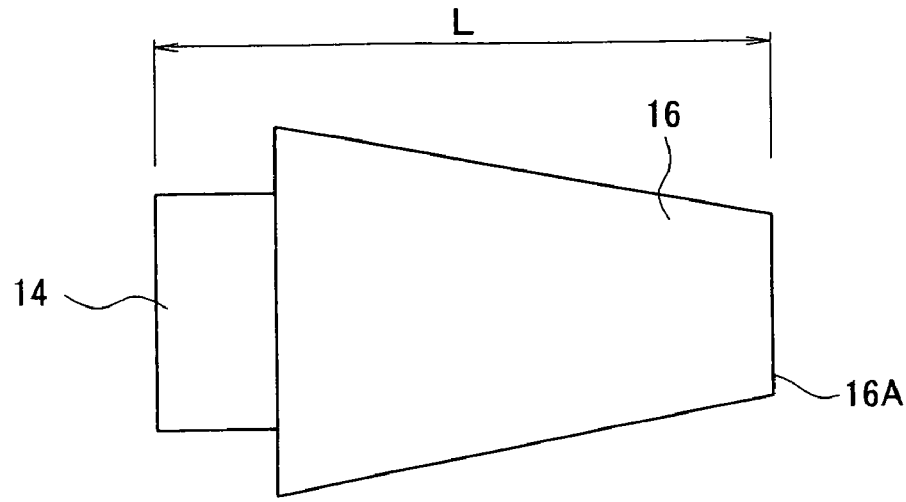
1/2 WAVELENGTH
(HALF-WAVELENGTH)
1 WAVELENGTH
(2 TIMES OF HALF
-WAVELENGTH)
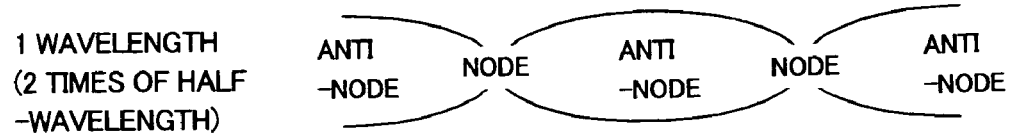
3/2 WAVELENGTH
(3 TIMES OF HALF
-WAVELENGTH)
N/2 WAVELENGTH
(N TIMES OF HALF
-WAVELENGTH)
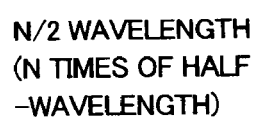

ULTRASONIC WASHING DEVICE

TECHNICAL FIELD

The present invention relates to a washer utilizing ultrasonic vibration, and especially relates to an ultrasonic washer for washing an object to be washed or a portion to be washed by spreading washing from a nozzle, to which vibration energy due to ultrasonic wave is propagated.

BACKGROUND ART

For example, in Japanese Laid-Open Patent Publication No. 6-218337, an ultrasonic washer 520 as shown in FIG. 37 is proposed for washing an object to be washed or a portion to be washed by spraying washing from a nozzle, to which vibration energy due to ultrasonic wave is applied.

The conventional ultrasonic washer 520 is comprised of a driving circuit 521, an ultrasonic transducer 522 driven by the driving circuit 521, an ultrasonic wave propagation member 523 for propagating ultrasonic vibration generated by the ultrasonic transducer 522, a cone 524 connected to the ultrasonic wave propagation member 523, a nozzle 525 connected to the cone 524 and serving as a horn to which ultrasonic wave is transmitted through the ultrasonic wave propagation member 523 and the cone 524, a water supply pipe 526 for supplying washing to an inside the nozzle 525, and so on. Since a plurality of flow passages is formed in the inside of the nozzle toward an opening at an end thereof, the ultrasonic vibration propagated to the nozzle 525 is further propagated to the washing while the washing passes through the flow passages. Then, the washing to which the ultrasonic vibration is propagated is sprayed from the opening at the end of the nozzle 525. Since the ultrasonic washer 520 is non-contact type, it is possible to wash a portion to be washed where a surface irregularity is larger.

In the conventional ultrasonic washer 520, the ultrasonic vibration generated by the ultrasonic transducer 525, however, is propagated to the nozzle 525 through the ultrasonic wave propagation member 523 and the cone 524, and further propagated to the washing from side walls of the flow passages of the nozzle 525 while the washing passes through the flow passages of the nozzle 525. Therefore, since transmission efficiency of the ultrasonic vibration is lower, when output power of the ultrasonic transducer 525 is smaller, there is a possibility that enough quantity of bubble is not generated the washing sprayed from the nozzle 525, and enough detergency due to cavitation effect is not provided. On the other hand, when the output power of the ultrasonic transducer 522 is made too high, there is a possibility that the washing becomes mist like a supersonic humidifier, and enough detergency is not provided.

Furthermore, the conventional ultrasonic washer 520 is a large-scale ultrasonic washer for washing, for example, a side wall of establishment, as described in the Publication gazette, in which the driving circuit 521 is independently provided from a main body, so that it has a configuration not suitable to be used on hand by a user.

DISCLOSURE OF INVENTION

A purpose of the present invention is, in an ultrasonic washer for washing an object to be washed or a portion to be washed by spraying washer thereto (SIC), to provide an ultrasonic washer, which can propagate ultrasonic vibration generated by an ultrasonic transducer to washing efficiently, enough detergency can be obtained corresponding to characteristics or dirt condition of an object to be washed or a portion to be washed by optimizing an output power of the ultrasonic transducer, thereby the object to be washed or the portion to be washed can be washed efficiently.

Furthermore, another purpose of the present invention is to provide an ultrasonic washer which can be used easily by a user on a hand, for example, when manicure applied to nails is peeled off, or when plaque adhered on teeth is removed.

For achieving the above-mentioned purposes, an ultrasonic washer in accordance with an aspect of the present invention comprises a housing having a main body and a nozzle unit, a water supply pipe for supplying washing to a cavity of said nozzle unit, an ultrasonic transducer contained in an inside of the main body of said housing and generating ultrasonic vibration, a driving circuit contained in the inside of the main body of said housing and droving the ultrasonic transducer, and an ultrasonic wave propagation member provided for protruding into the inside of said main body and into the cavity of said nozzle unit, said ultrasonic transducer being fixed on a portion thereof in said main body side, and directly propagating the ultrasonic vibration generated by the ultrasonic transducer to the washing supplied to the cavity of said nozzle unit from an end face thereof in said nozzle unit side.

According to such a configuration, the ultrasonic vibration generated by the ultrasonic transducer is propagated to the washing through only the ultrasonic wave propagation member, so that energy loss becomes smaller and the efficiency of propagation of the ultrasonic vibration becomes higher. Thus, even when an output power of the ultrasonic transducer is made smaller in comparison with the conventional ultrasonic washer, enough detergency can be obtained. Therefore, by adjusting the output power of the ultrasonic transducer optimally corresponding to characteristics or dirt condition of an object to be washed or a portion to be washed, it is possible to wash the object to be washed or the portion to be washed efficiently without atomization of the washing. Furthermore, it is easily used by a user by hand, because operationality is improved without code interfering to take the driving circuit contained in the main body of the housing.

BRIEF DESCRIPTION OF DRAWINGS

FIG. 5 is a diagram schematically showing a relationship between a length that an ultrasonic transducer and an ultrasonic wave propagation member in the second embodiment are joined and a wavelength of ultrasonic standing wave oscillation.

BEST MODE FOR CARRYING OUT THE INVENTION

First Embodiment

Figure 1:
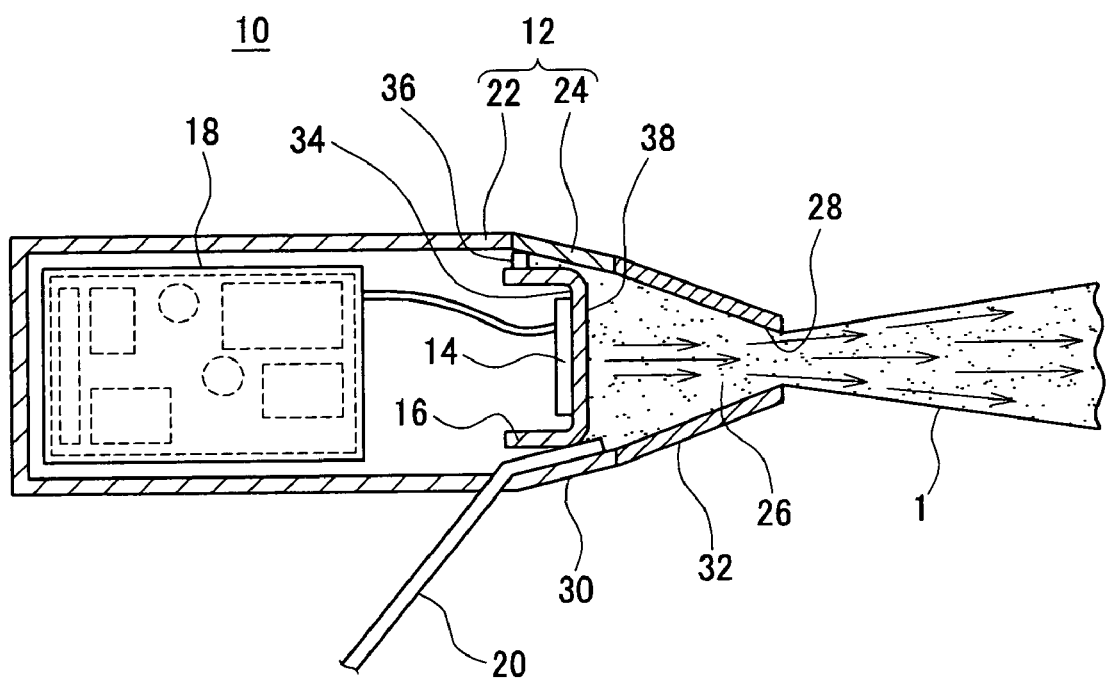
FIG. 1 is a sectional view showing a constitutional example of an ultrasonic washer in accordance with in a first embodiment of the present invention.

A configuration of an ultrasonic washer 10 in accordance with in a first embodiment of the present invention is shown in FIG. 1. The ultrasonic washer 10 comprises a housing 12 formed of an insulative synthetic resin. An ultrasonic transducer 14, an ultrasonic wave propagation member 16 to which the ultrasonic transducer 14 is joined, a driving circuit 18 for driving the ultrasonic transducer 14, and so on are provided in an inside of the housing 12.

The housing 12 is comprised of a substantially tube shaped main body 22, a nozzle unit 24 coupled with an end of the main body 22, and so on. A water supply pipe 20 is connected to the nozzle unit 24, so that washing is supplied to a cavity 26 of the nozzle unit 24 from a washing tank which is not illustrated. The nozzle unit 24 has, for example, a frustum shape, and is formed so that the cross-sectional area thereof becomes smaller as approaching to a front end of the housing 12. Furthermore, a front end of the nozzle unit 24 is opened so as to serve as a splay opening 28 of washing.

The ultrasonic wave propagation member 16 is provided in a manner to protrude to respective of the inside of the main body 22 and the cavity 26 of the nozzle unit 24. Therefore, ultrasonic wave generated by the ultrasonic transducer 14 is directly propagated to the washing filled in the cavity 26 of the nozzle unit 24 from the ultrasonic wave propagation member 16. Besides, the nozzle unit 24 is comprised of an inside member 30 fixed on the main body 22 and an outside member 32 which can be put on and taken off for the inside member 30, for example, to wash the cavity 26. Alternatively, it is possible to constitute that the inside member 30 and the outside member 32 of the nozzle unit 24 are integrally formed and can be taken off for the main body 22.

Since the nozzle unit 24 of the housing 12 has a frustum shape that cross-sectional area becomes gradually smaller toward the splay opening 28 from the ultrasonic wave propagation member 16 at the bottom thereof, the ultrasonic vibration transmitted from the ultrasonic wave propagation member 16 is converged to the center portion, and concentrated to the splay opening 28. As a result, energy of ultrasonic vibration is efficiently propagated to the washing splayed from the splay opening 28. In this way, the ultrasonic wave propagation member 16, to which the ultrasonic transducer 14 is joined, and which transmits the ultrasonic wave generated by the ultrasonic transducer 14, is directly contacted to the washing so as to propagate the ultrasonic vibration to the washing, so that the transmission efficiency of the ultrasonic vibration becomes much higher in comparison with the above-mentioned conventional ultrasonic washer. Therefore, it is possible to obtain an enough detergency corresponding to characteristics or dirt condition of an object to be washed or a portion to be washed by optimizing an output power of the ultrasonic transducer 14, so that the object to be washed or the portion to be washed can be washed effectively.

The ultrasonic transducer 14 uses a piezoelectric transducer made of a ceramics material such as detergency or a quartz crystal, and generates vibration with utilizing transformation in thickness direction of the piezoelectric transducer. The ultrasonic wave propagation member 16 is made of a metal material in a bowl shape, and the ultrasonic transducer 14 is fixed to an inner bottom face 34 thereof. A supporting portion 36 of flange shape protruding outward from a side face forming the bowl shape is formed in the vicinity of the end portion of the opening side of the ultrasonic wave propagation member 16, so that it is fixed in the inside of the housing 12 so that an outer bottom face 38 faces the spray opening 28. As a result, the ultrasonic wave propagation member 16 and the supporting portion 36 constitute a part of a bottom wall of the nozzle unit 24. For a material of the ultrasonic wave propagation member 16, a light metal such as aluminum, and a light alloy such as aluminum alloy or titanium alloy can be used. It is desirable that these materials are treated with rustproof such as alumite treatment or ion plating treatment on the surfaces thereof from a viewpoint of rust prevention.

The driving circuit 18 is implemented by mounting electronic components constituting an oscillating circuit or the like on a printed circuit board, and driven by a battery or a commercial power supply which is not illustrated. The driving circuit 18 adjusts oscillation frequency or drive voltage of the ultrasonic transducer 14 depending on switching operation by a user. The water supply pipe 20 is connected to a washing tank or a faucet of water service which is not illustrated, and supplies the washing such as water or soapy water to the cavity 26 of the nozzle unit 24 with a predetermined quantity of supply per unit of time. Besides, the quantity of supply of the washing can be adjusted by controlling a power of pump provided between the tank and the water supply pipe 20 or an aperture quantity of the faucet of water service.

Subsequently, an operation of the ultrasonic washer 10 is described. When the washing 1 is supplied with a constant quantity of supply per unit time to the cavity 26 of the nozzle unit 24 through the water supply pipe 20, the washing 1 is splayed with a constant pressure from the splay opening 28 after the washing 1 is filled in the cavity 26. At that time, ultrasonic vibration with a predetermined frequency is generated by the ultrasonic transducer 14 by driving the driving circuit 18. The ultrasonic vibration generated by ultrasonic transducer 14 is propagated into the washing 1 filled in the cavity 26 of the nozzle 24 through the ultrasonic wave propagation member 16. Then, the washing 1 is splayed from the spray opening 28 with receiving the energy due to the ultrasonic vibration. Since the washing 1 includes a lot of minute bubbles generated by the ultrasonic vibration, when the washing 1 is splayed to an object to be washed or a portion to be washed, the minute bubbles in the washing explode, and localized impulse waves called cavitation occur. Heavy dirt (greasy dirt) adhered on the object to be washed or the portion to be washed is forcibly torn off and removed by the impulse waves. Therefore, higher effective detergent can be obtained in comparison with a case of merely spraying the washing.

The driving circuit 18 has a function for controlling an oscillation frequency of the ultrasonic transducer 14. By setting the oscillation frequency of the ultrasonic transducer 14 to be lower, for example several kHz to several hundreds kHz extent, the washing to which ultrasonic vibration of lower frequency is propagated is splayed. In this case, relatively large bubbles are generated, and the impulse waves generated when the bubbles explode are larger. Therefore, it is suitable for removing the heavy dirt of high adhesion. On the other hand, by setting the oscillation frequency of the ultrasonic transducer 14 to be higher, for example several MHz to several hundreds kHz extent, the washing to which ultrasonic vibration of higher frequency is propagated is splayed. In this case, since the generated bubbles are smaller, the impulse waves at the explode of the bubbles are smaller, and it is suitable for removing light dirt of low adhesion while reducing damage to give the object to be washed or the portion to be washed is made smaller. In this way, an optimum detergency can be obtained by adjusting the oscillation frequency of the ultrasonic transducer 14 corresponding to the characteristics or dirt condition of the object to be washed or the portion to be washed by.

Furthermore, the driving circuit 18 has a function to control the output power of the ultrasonic wave of the ultrasonic transducer 14. Specifically, the output power of the ultrasonic wave of the ultrasonic transducer 14 is adjusted by varying driving voltage supplied to the ultrasonic transducer 14. When the output power of the ultrasonic wave of the ultrasonic transducer 14 is raised, the ultrasonic vibration having larger amplitude is propagated to the washing. Action such as oscillation, disturbance, defoaming, and emulsification of the washing in itself contributes to the ultrasonic washing further to the above-mentioned cavitation by bubbles. In this case, since the ultrasonic vibration with larger amplitude is propagated to the washing, the amplitude of the vibration of the washing in itself becomes larger, and the detergency rises. Therefore, it is suitable to remove the heavy dirt with high adhesion. On the other hand, when the output power of the ultrasonic transducer 14 is made smaller, the amplitude of the ultrasonic vibration propagated to the washing becomes smaller, and the detergency falls. Therefore, it is suitable to remove light dirt with weak adhesion.

Furthermore, the driving circuit 18 has an intermittent driving function which can drive the ultrasonic transducer 14 intermittently and adjust the frequency for intermittent driving. Specifically, the frequency of the intermittent driving is adjusted by varying a period for supplying driving electric power and a period not for supplying driving electric power to the ultrasonic transducer. When the frequency of the intermittent driving is lower, impact force due to the washing splayed from the splay opening 28 becomes relatively strong, and detergency rises. On the other hand, when the frequency of the intermittent driving is higher, the impact force due to the washing splayed from the splay opening 28 becomes relatively weak, and detergency falls. Furthermore, it is possible to control a fever of the object to be washed or the portion to be washed to which the washing propagated the ultrasonic vibration is splayed by adjusting the frequency of then intermittent driving of the ultrasonic transducer 14. In particular, when the object to be washed or the portion to be washed is a living body, a body temperature of a neighborhood of the portion to which the washing is splayed rises. Therefore, it is possible to perform the optimum washing corresponding to the region to be washed or physical condition of a user by not only intermittently driving the ultrasonic transducer 14 but also adjusting the frequency.

In this way, since the driving circuit 18 can optimize the output power of the ultrasonic transducer 14 depending on the switching operation by the user, it is possible to obtain enough detergency corresponding to the characteristics or dirt condition of the object to be washed or the portion to be washed without raising the output power of the ultrasonic transducer 14 more than requires. In particular, when the object to be washed or the portion to be washed is a part of living body, the ultrasonic transducer 14 is not required very large output power, so that it is possible to provide an ultrasonic washer which can be used with holding by hand for tearing off the manicure applied to nails or removing the plaque on teeth.

Figure 2A:
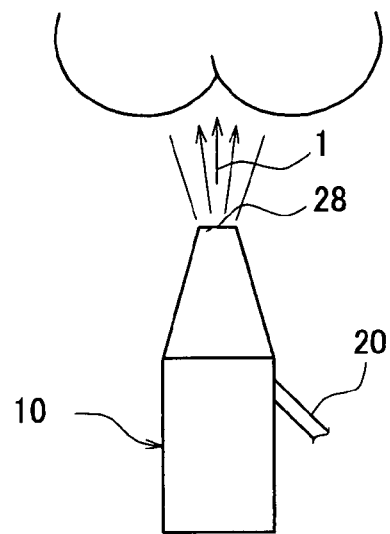
FIGS. 2A to 2F are drawings each showing an example of application of the ultrasonic washer which splays washing.
Figure 2B:
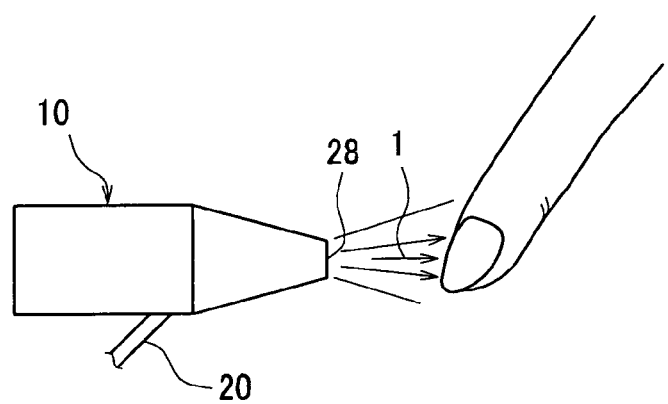
Figure 2C:
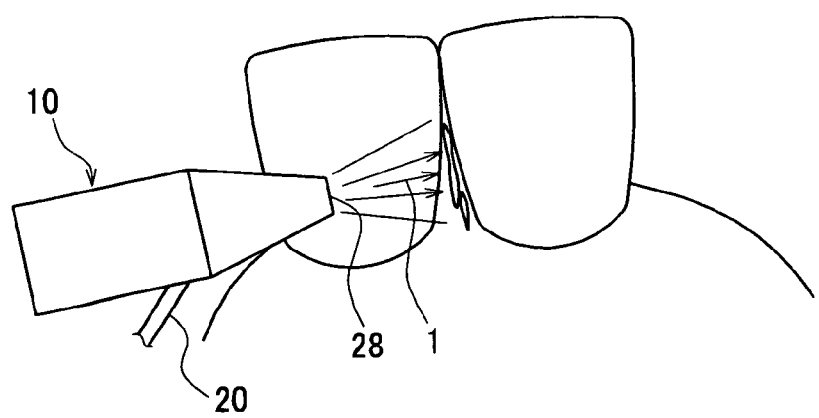
Figure 2D:
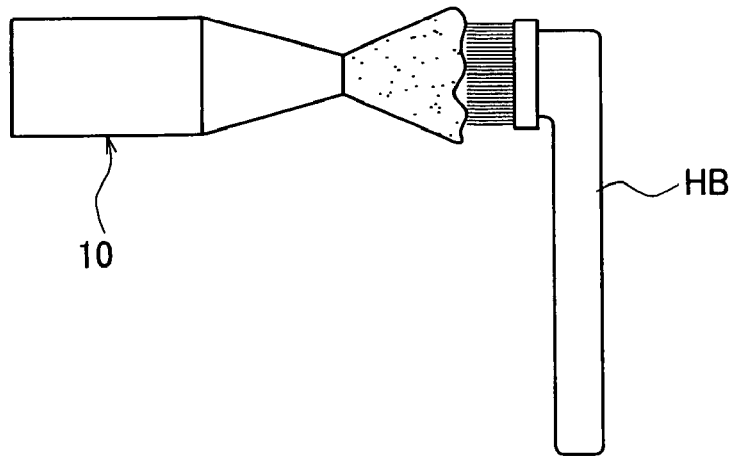
Figure 2E:
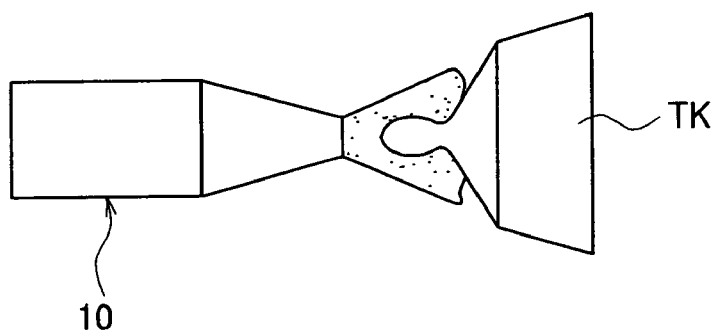
Figure 2F:
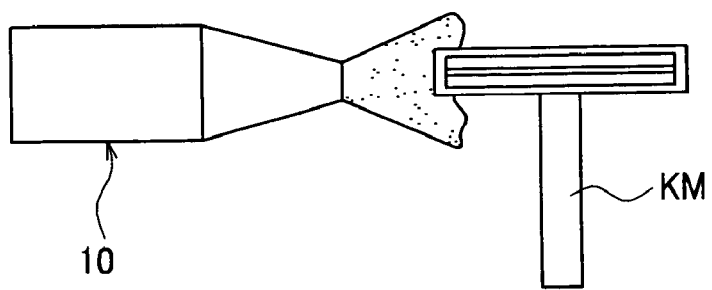

Applications of the ultrasonic washer 10 are shown in FIG. 2A to FIG. 2F. FIG. 2A shows an example that the ultrasonic washer 10 is fixed on a seat in a restroom used as a bidet for washing the vicinity of anus. FIG. 2B shows an example that the ultrasonic washer 10 is used as a beauty utensil for removing the manicure adhered on a surface of a nail, or the like. FIG. 2C shows an example that the ultrasonic washer 10 is used as an oral cavity washing tool for removing the plaque on teeth. FIG. 2D to FIG. 2F show examples for washing articles (daily necessaries) which need to keep sanitary conditions such as a toothbrush, a nipple of a baby-bottle, and a shaver. In these ways, the ultrasonic washer 10 splays the washing to the object to be washed or the portion to be washed under non-contact condition, so that it is possible to wash the portion to be washed where the convex and concave of the surface is larger. Besides, it is needless to say that a quantity of the washing to be splayed and the power of the ultrasonic transducer are respectively set to be optimum values corresponding to the application.

Figure 3:
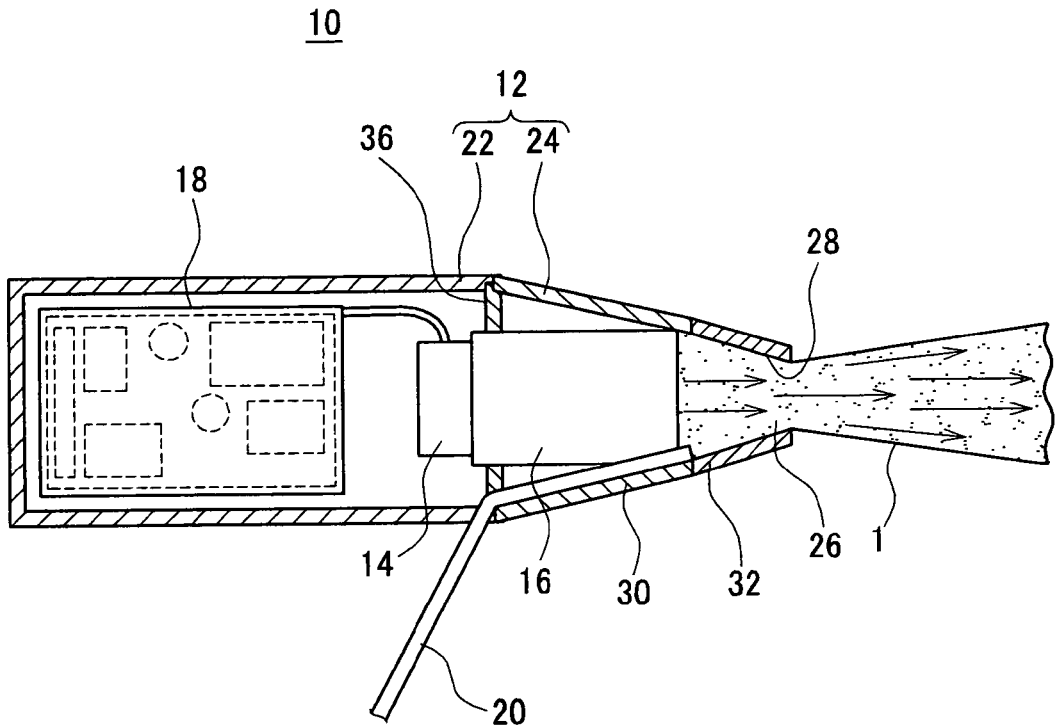
FIG. 3 is a sectional view showing another constitutional example of the ultrasonic washer in accordance with in the first embodiment.

Subsequently, a modified example of the first embodiment is shown in FIG. 3. In the ultrasonic washer 10 shown in FIG. 3, the ultrasonic wave propagation member 16 is substantially cylindrical shape, and protruded largely in the cavity 26 of the nozzle unit 24. Since the shape of the nozzle unit 24 is formed substantially frustum so that the cross-sectional area becomes smaller as approaching to the splay opening 28, the ultrasonic vibration transmitted from the ultrasonic wave propagation member 16 is concentrated to the splay opening 28, and the energy of the ultrasonic vibration is efficiently propagated to the washing splayed from the splay opening 28. By such a configuration, substantially the same effect as above can be obtained.

Second Embodiment

Figure 4:
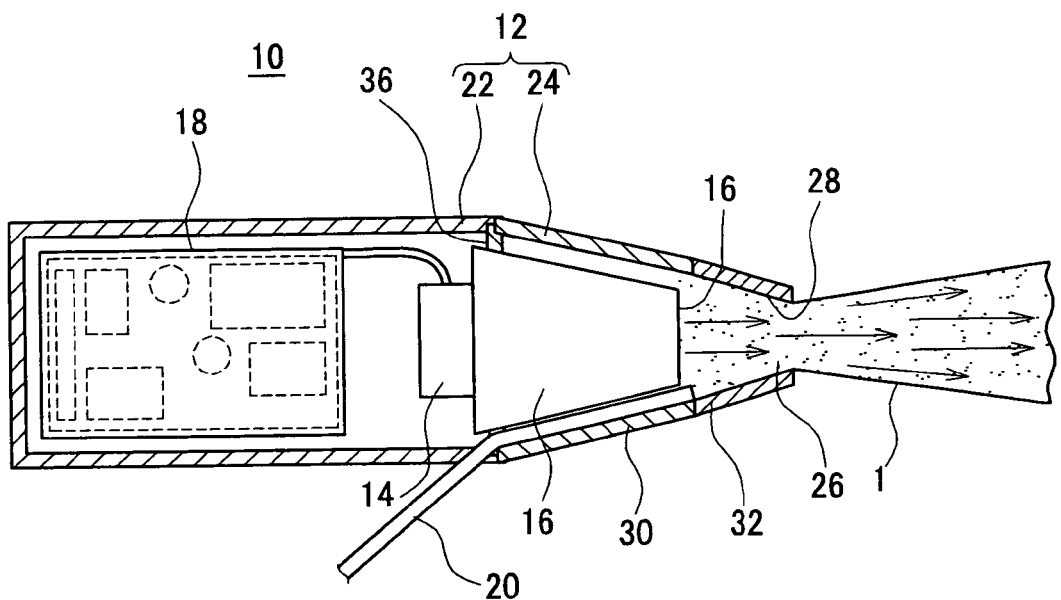
FIG. 4 is a sectional view showing a constitutional example of an ultrasonic washer in accordance with in a second embodiment of the present invention.

Subsequently, a configuration of an ultrasonic washer 10 in accordance with a second embodiment of the present invention is shown in FIG. 4. Besides, with respect to the portions substantially the same as those in the above first and second (SIC) embodiments, description of them is omitted, and only dissimilarity is described.

As shown in FIG. 4, in the ultrasonic washer 10 in accordance with in the second embodiment, the ultrasonic wave propagation member 16 is substantially frustum shape, and a portion protruding into the cavity 26 of the nozzle unit 24 is formed so that the cross-sectional area of it in a direction parallel to a joint face with the ultrasonic transducer 14 becomes gradually smaller as approaching to the end portion of the nozzle, that is, an ultrasonic wave emission face 16A. Furthermore, the shape of the nozzle unit 24 is formed substantially frustum so that the cross-sectional area of it becomes smaller as approaching to the splay opening 28. Therefore, the ultrasonic vibration generated by the ultrasonic transducer 14 is converged at the center portion by the substantially frustum-shaped ultrasonic wave propagation member 16, and it is efficiently propagated into the washing in the cavity 26. Furthermore, the ultrasonic vibration transmitted from the ultrasonic wave propagation member 16 is concentrated to the splay opening 28, so that the ultrasonic vibration is efficiently propagated to the washing splayed from the splay opening 28.

Subsequently, the ultrasonic transducer 14 and the ultrasonic wave propagation member 16 are explained. As shown in FIG. 5, an overall length L of a joined matter of the ultrasonic transducer 14 and the ultrasonic wave propagation member 16 is set to be an integral multiplication of a half-wavelength, that is, ½ of a wavelength of an ultrasonic standing wave oscillation. In FIG. 5, positions of node and antinode of oscillation in cases of L=½ wavelength, L=1 wavelength, L=3/2 wavelength . . . L=N/2 wavelength are shown sequentially from the top. In this way, by setting the overall length L of the joined matter of the ultrasonic transducer 14 and the ultrasonic wave propagation member 16 is set to be an integral multiplication of the half-wavelength of the ultrasonic standing wave oscillation, the end face of the ultrasonic wave propagation member 16, that is, the ultrasonic wave emission face 16A is located at a portion of antinode where the amplitude becomes the largest, so that it is possible to propagate the ultrasonic vibration to the washing efficiently.

Figure 6:
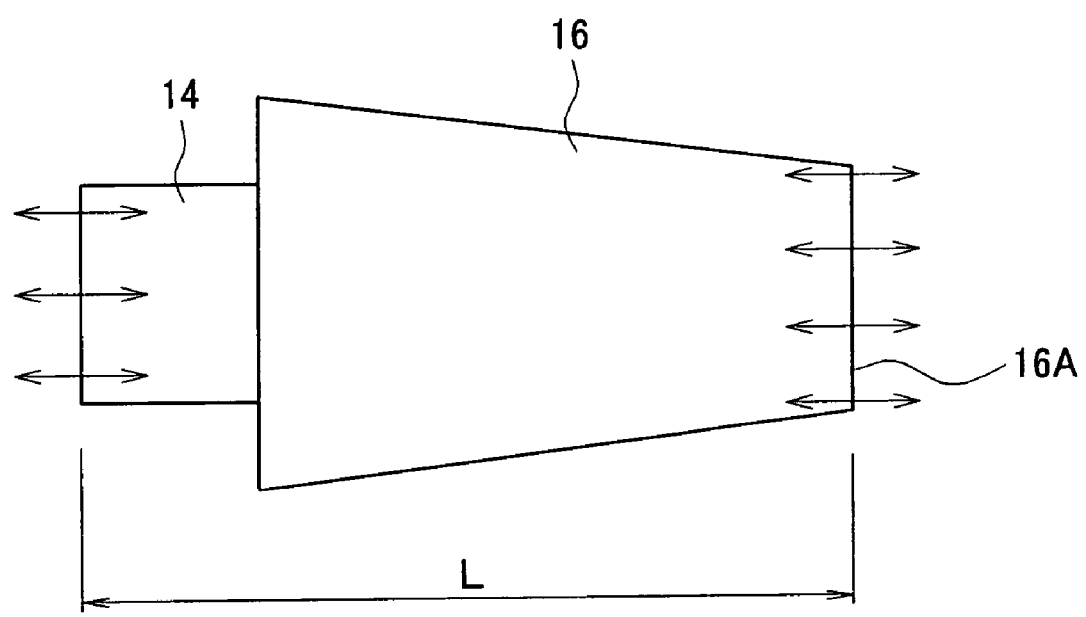
FIG. 6 is a diagram schematically showing a condition that the ultrasonic wave propagation member is vibrated with using oscillation in thickness direction of the ultrasonic transducer in the second embodiment.

FIG. 6 schematically shows a condition that the ultrasonic wave propagation member 16 is vibrated with using the oscillation of the ultrasonic transducer 14 in the thickness direction thereof. In this way, the ultrasonic vibration is transmitted in a direction perpendicular to the ultrasonic wave emission face 16A of the ultrasonic wave propagation member 16 by generating the ultrasonic vibration utilizing expansion and contraction of the ultrasonic transducer 14 in the thickness direction thereof. Therefore, the ultrasonic vibration can be propagated to the washing in the cavity 26 of the nozzle unit 24 from the ultrasonic wave emission face 16A of the ultrasonic wave propagation member 16 efficiently.

Figure 7A:
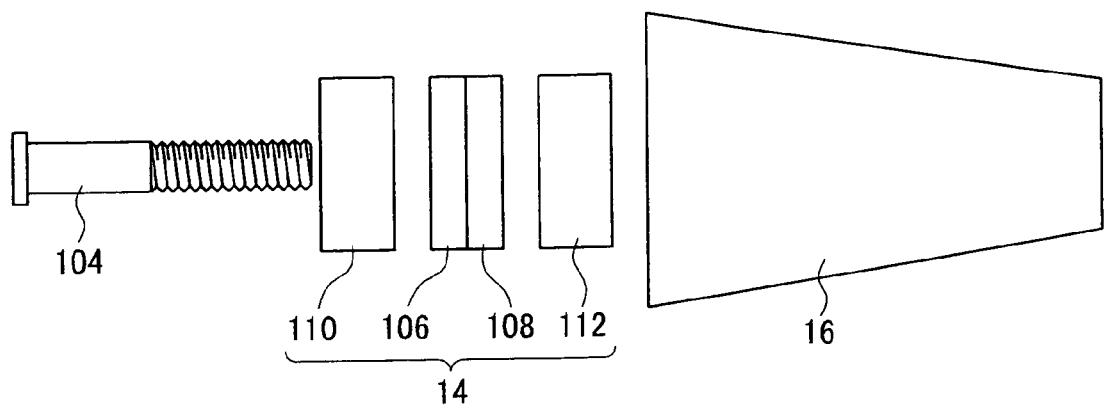
FIG. 7A is a view showing a condition before assembling the ultrasonic transducer in the second embodiment.
Figure 7B:
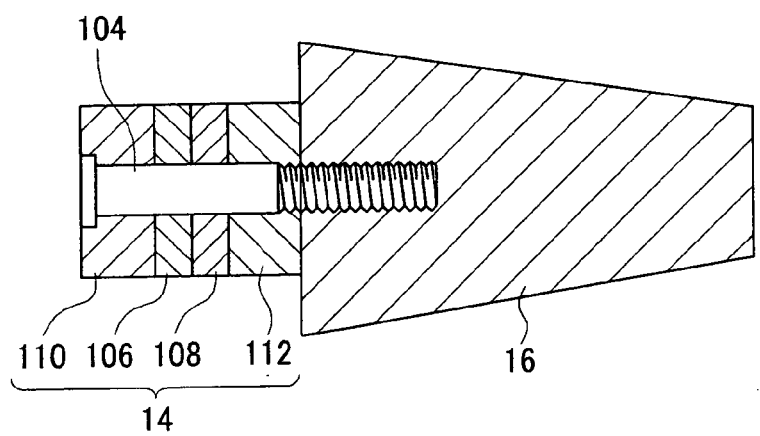
FIG. 7B and FIG. 7C are respectively sectional view and an outside view of a condition that the ultrasonic transducer and the ultrasonic wave propagation member are assembled.
Figure 7C:
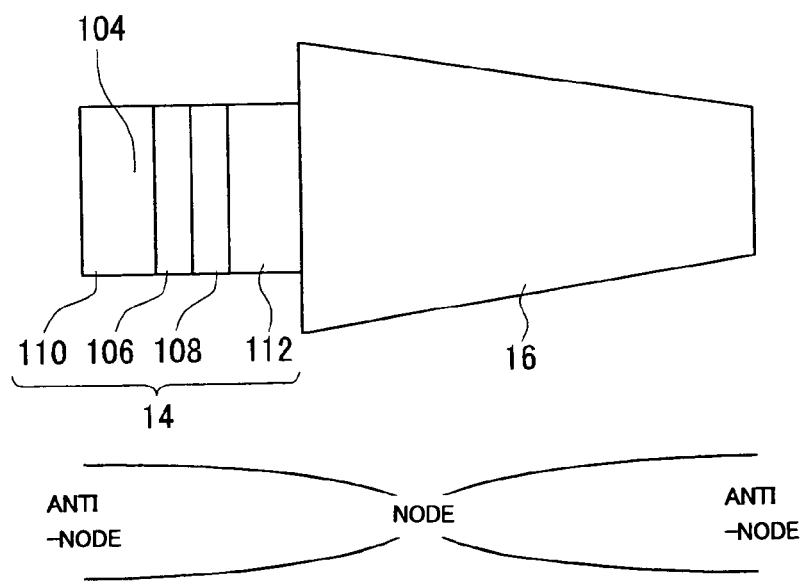

Subsequently, specific configurations of the ultrasonic transducer 14 and the ultrasonic wave propagation member 16 are described. FIG. 7A shows a condition before assembling the ultrasonic transducer 14 and the ultrasonic wave propagation member 16 and FIG. 7B and FIG. 7C show the condition that assembled them. As can be seen from these figures, the ultrasonic transducer 14 and the ultrasonic wave propagation member 16 constitutes a bolting type Langevin transducer. The ultrasonic transducer 14 is constituted so that two transducers 106 and 108 which are formed by, for example, lamination of piezoelectric ceramics are intervened between two wavelength adjustment members 110 and 112, and fixed on the ultrasonic wave propagation member 16 by a bolt 104.

The wavelength adjustment members 110 and 112 are used for adjusting resonance frequency of the ultrasonic transducer 14, and made of a light metal such as aluminum or a light alloy such as aluminum alloy. Then, after assembled as shown in FIG. 7B and FIG. 7C, the resonance frequency of the ultrasonic transducer 14 is adjusted by shaving a part of the wavelength adjustment member(s) 110 and/or 112 while the ultrasonic transducer 14 is actually oscillated. Besides, it is preferable to provide rust proof treatment on surfaces of the wavelength adjustment members 110 and 112 from the viewpoint of rust prevention.

Figure 8A:
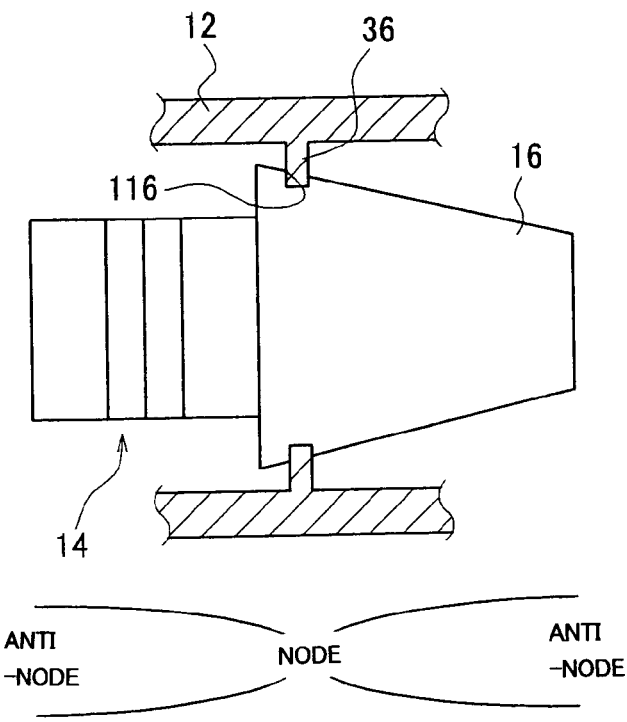
FIG. 8A and FIG. 8B are views each showing a fixing structure of a bolting type Langevin transducer comprised of an ultrasonic transducer and an ultrasonic wave propagation member.
Figure 8B:
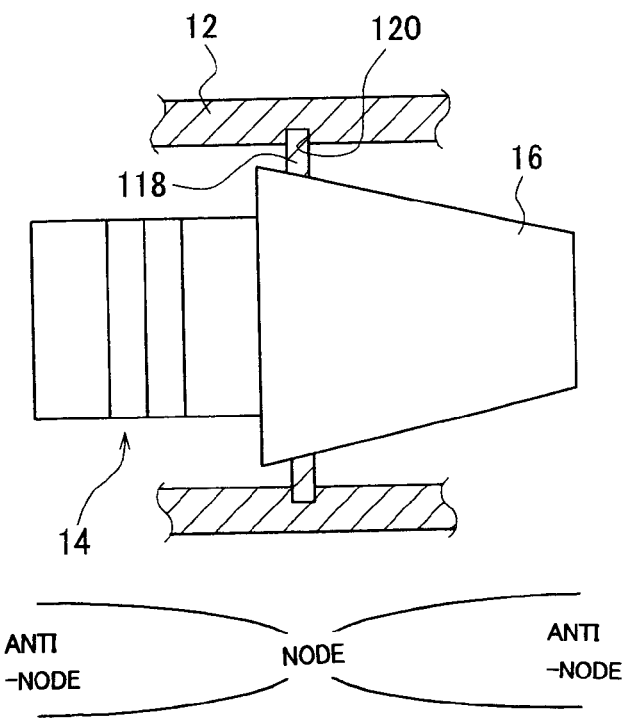

Fixing structures of the bolting type Langevin transducer comprised of the ultrasonic transducer 14 and the ultrasonic wave propagation member 16 are shown in FIG. 8A and FIG. 8B.

In these fixing structures, the ultrasonic wave propagation member 16 is fixed to housing 12 at a position of a node of the ultrasonic standing wave oscillation. In the example shown in FIG. 8A, a supporting portion 36 of flange shape protruding inwardly is formed on an inner peripheral face of the housing 12, and a concave portion 116 is formed at a position on an outer peripheral face of the ultrasonic wave propagation member 16 of substantially frustum shape of a node of ultrasonic standing wave oscillation. Then, by engaging the supporting portion 36 with the concave portion 116, the bolting type Langevin transducer comprised of the ultrasonic transducer 14 and the ultrasonic wave propagation member 16 is mounted on the housing 12. In the example shown in FIG. 8B, a supporting portion 118 is protruded outward from a position on an outer peripheral face of the ultrasonic wave propagation member 16 of substantially frustum shape of a node of ultrasonic standing wave oscillation, and it is engaged with a concave portion 120 formed on an inner peripheral face of the housing 12.

In this way, it is possible to lower an affect due to the ultrasonic transducer 14 and the ultrasonic wave propagation member 16 affecting to the ultrasonic vibration and to propagate the ultrasonic vibration to the washing efficiently with lowering energy loss by fixing the bolting type Langevin transducer comprised of the ultrasonic transducer 14 and the ultrasonic wave propagation member 16 at a position of a node of the ultrasonic standing wave oscillation. Besides, since the vibration remains a little at the position of the node of the ultrasonic standing wave oscillation, it is possible to intervene an elastic member between the supporting portion 36 and the concave portion 11 in FIG. 8A and between the supporting portion 118 and the concave portion 120 in FIG. 8B. Furthermore, these fixing structures are not limited to the bolting type Langevin transducer, and it is needless to say that it can apply to a transducer having another configuration.

Figure 9A:
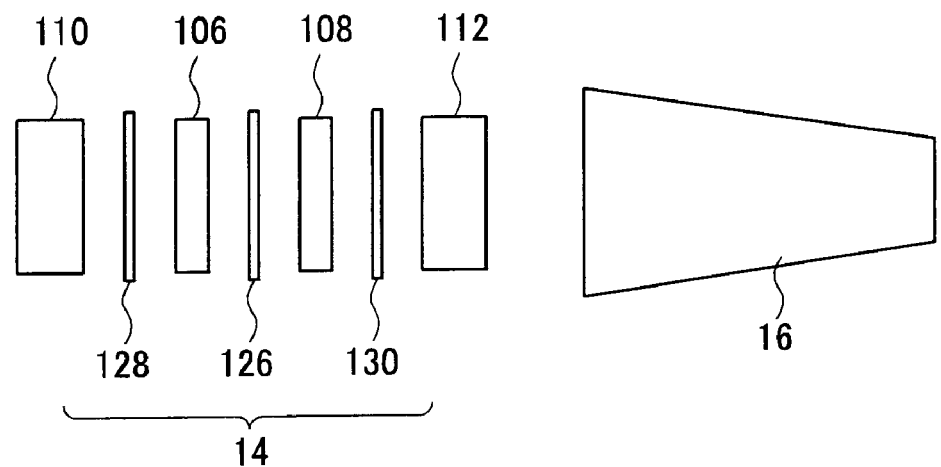
FIG. 9A is a side view showing a more specific structure of the bolting type Langevin transducer.
Figure 9B:
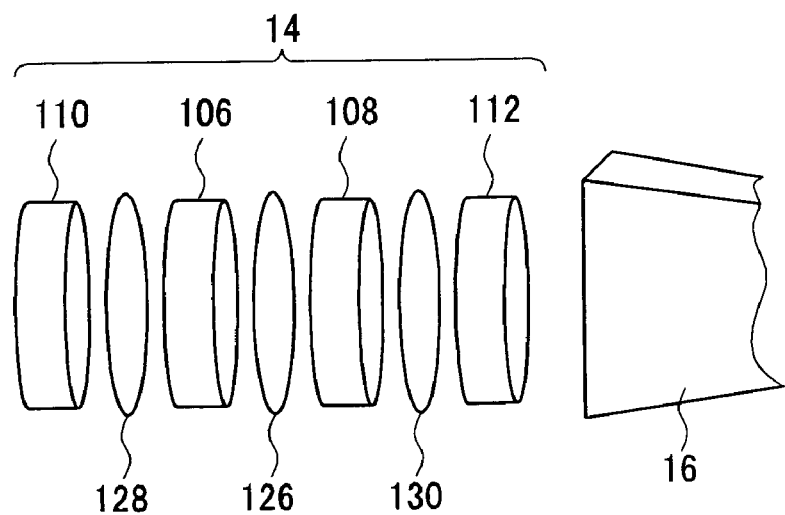
FIG. 9B is an exploded perspective view thereof.
Figure 10A:
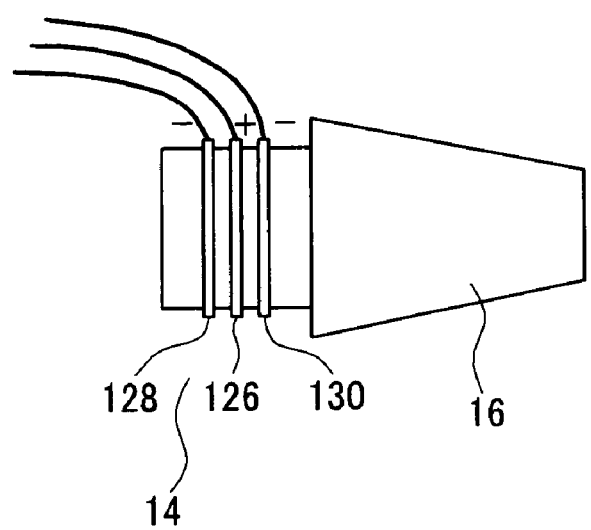
FIG. 10A and FIG. 10B are views each showing a wiring example of the ultrasonic transducer.
Figure 10B:
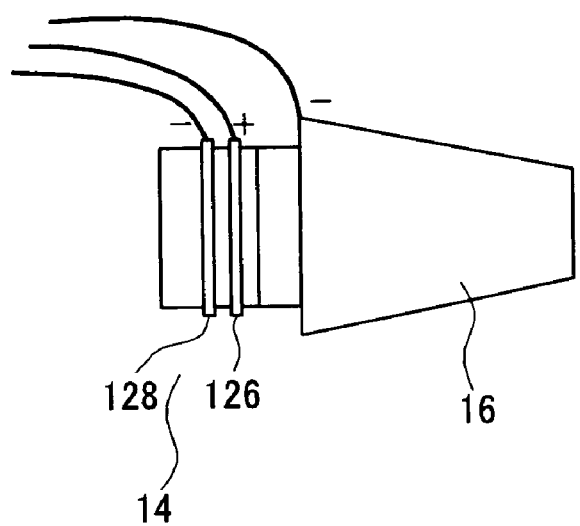

More specific configuration of the bolting type Langevin transducer is shown in FIG. 9A, FIG. 9B, FIG. 10A and FIG. 10B. FIG. 9A is an exploded side view of the bolting type Langevin transducer, and FIG. 9B is an exploded perspective view thereof. Furthermore, FIG. 10A and FIG. 10B are views showing wiring connections. Besides, a bolt for fixing the ultrasonic transducer 14 to the ultrasonic wave propagation member 16 is omitted in these figures.

In this constitutional example, conductive sheets 126, 128 and 130 made of such as a metal are respectively disposed between two transducers 106 and 108, between the transducer 106 and the wavelength adjustment member 110, and between the transducer 108 and the wavelength adjustment member 112. As shown in FIG. 10A, the conductive sheet 126 at the center is connected to plus potential, and the conductive sheets 128 and 130 at both ends are connected to minus potential, so that electric shock is prevented by the ultrasonic wave propagation member 16. Furthermore, it is possible to omit the conductive sheet 130 between the transducer 108 and the wavelength adjustment member 112, when the ultrasonic wave propagation member 16 is connected to minus potential, as shown in FIG. 10B.

By interleaving the transducers 106 and 108 between electrodes having high conductivity such as nickel or beryllium, the voltage drop due to electrode becomes smaller and a high voltage can be applied to the transducers 106 and 108, so that piezoelectric transducers 106 and 108 can be oscillated efficiently. Furthermore, by positioning a boundary between two transducers 106 and 108 serving as a driving source at a position of a node of the ultrasonic standing wave oscillation, the oscillation of the transducers 106 and 108 can transmit to the ultrasonic wave propagation member 16 efficiently.

Figure 11:
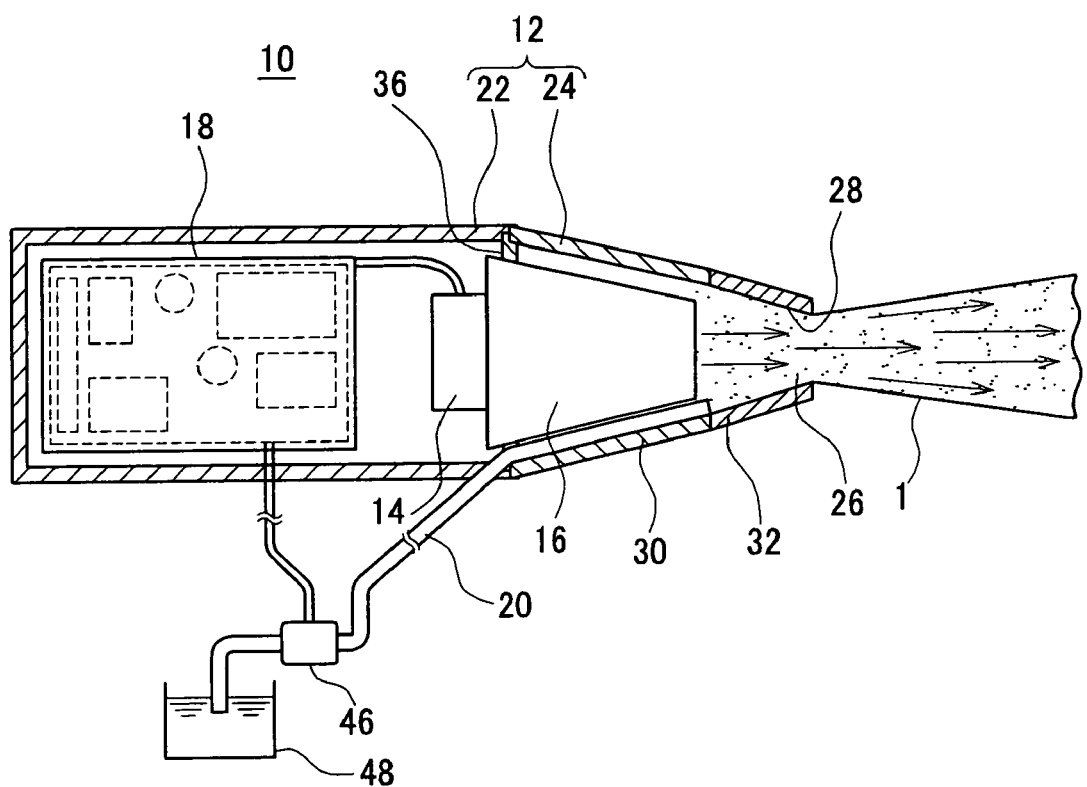
FIG. 11 is a sectional view showing another constitutional example of the ultrasonic washer in accordance with the second embodiment.
Figure 12A:
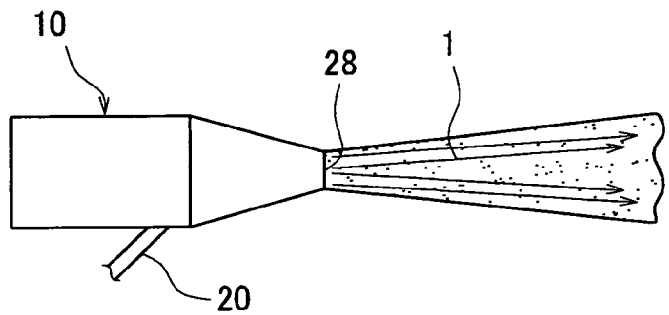
FIG. 12A and FIG. 12B are views respectively showing conditions for splaying of washing when a pump is continuously driven and intermittently driven.
Figure 12B:
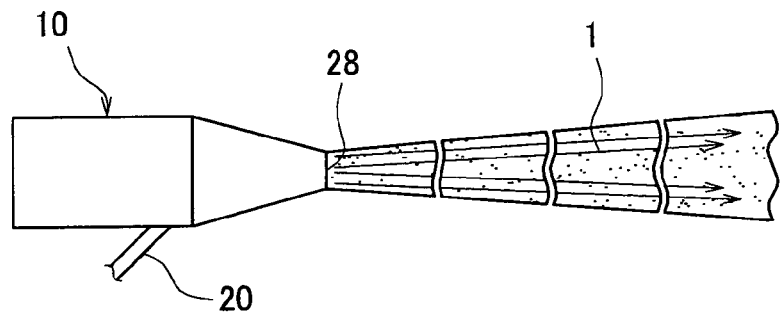

Subsequently, a constitutional example that a washing tank 48 and a pump 46 are connected to the water supply pipe 20 of the ultrasonic washer 10 shown in FIG. 4 is shown in FIG. 11. The pump 46 is driven in synchronism with the driving of the ultrasonic transducer 14 by, for example, the driving circuit 18. It is possible to splay the washing continuously from the splay opening 28 by continuously driving the pump 46, as shown in FIG. 12A. Alternatively, it is possible to splay the washing pulsatively from the splay opening 28 by intermittently driving the pump 46, as shown in FIG. 12B. In this way, it is possible to select the most suitable splay mode of the washing corresponding to user's preference or dirt condition of the object to be washed or the portion to be washed by constituting the splay mode of the washing changeable. Furthermore, it is possible to adjust the power of absorption of the pump 46, that is, the liquid quantity per unit time of the washing splayed from the splay opening 28 by adjusting, for example, drive voltage of the pump 46.

Besides, the pump 46 is not necessary driven by the driving circuit 18, and it may be constitute to be driven by a driving circuit provided independently. For example, when the ultrasonic washer 10 is used stationary as shown in FIG. 2A, it is preferable respectively to drive the ultrasonic transducer 14 by the driving circuit 18 and to drive the pump 46 by a pump driving circuit corresponding to control signals from a remote control device (not illustrated) at user's hand. Furthermore, when ultrasonic washer 10 is used on hand as shown in FIG. 2B and FIG. 2C, it is preferable that a switch is provided on a housing 12 of the ultrasonic washer 10 and the ultrasonic transducer 14 and the pump 46 are controlled by the driving circuit 18 corresponding to the switching operation by the user.

Figure 13:
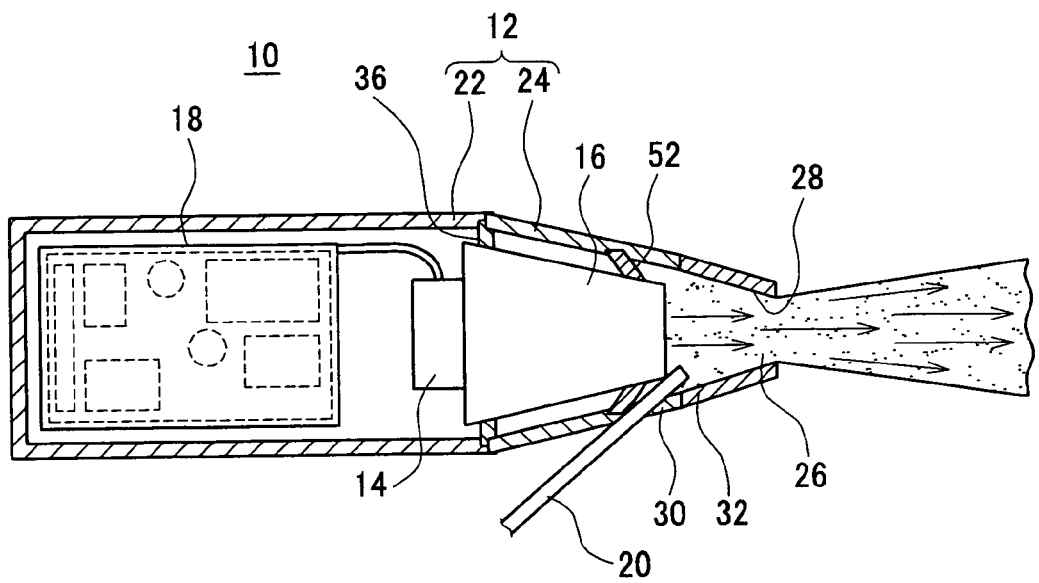
FIG. 13 is a sectional view showing still another constitutional example of the ultrasonic washer in accordance with the second embodiment.

Another modified example of the ultrasonic washer 10 is shown in FIG. 13. In the ultrasonic washer 10, a seal member 52 is provided between the inner peripheral surface of the inside member 30 of the nozzle unit 24 and an outer peripheral surface of the ultrasonic wave propagation member 16 so as to prevent wraparound of the washing supplied into the cavity 26 to slanted side face portion of the ultrasonic wave propagation member 16. In other words, the capacity of the cavity 26 is made smaller by the seal member 52.

For the seal member 52, it may be molded in a disc shape of an elastic material such as rubber, and closely adhered on respective of the inner peripheral surface of the inside member of the nozzle unit 24 and the side face of the ultrasonic wave propagation member 16. In that case, each element can be washed with disassembling separately when the nozzle unit 24 is taken off from the main body 22 and washed. Alternatively, the seal member subject 52 may be molded integrally with the inside member 30.

By providing the seal member 52 like this, although the configuration becomes complex and a number of elements increases, it is possible to reduce the energy loss of the ultrasonic vibration propagated to the washing from the side face of the ultrasonic wave propagation member 16.

Figure 14:
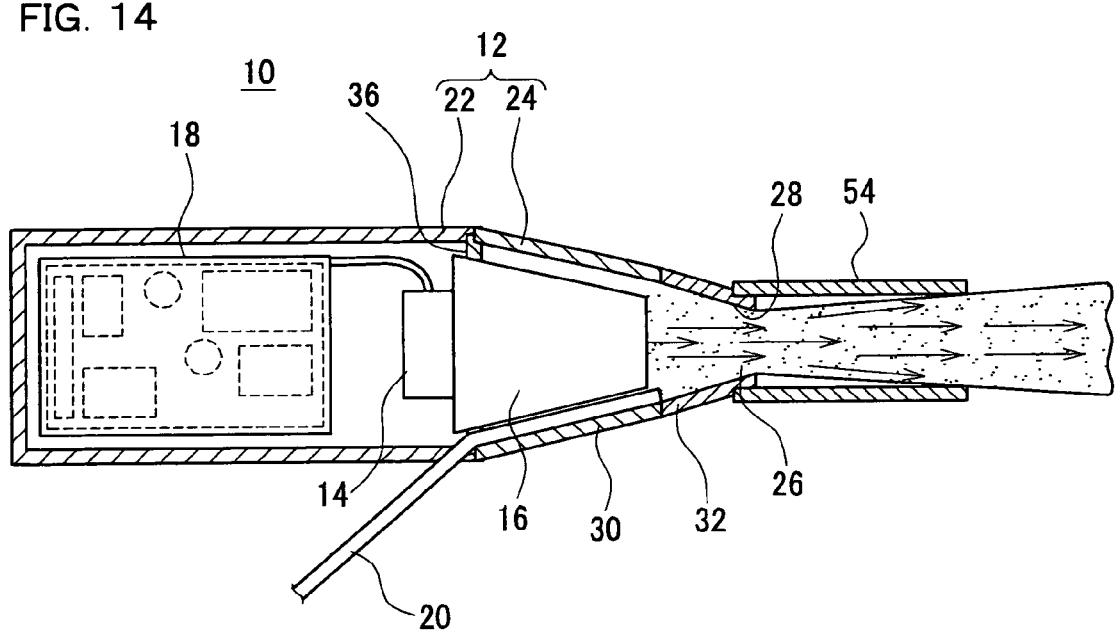
FIG. 14 is a sectional view showing still another constitutional example of the ultrasonic washer in accordance with the second embodiment.
Figure 15A:
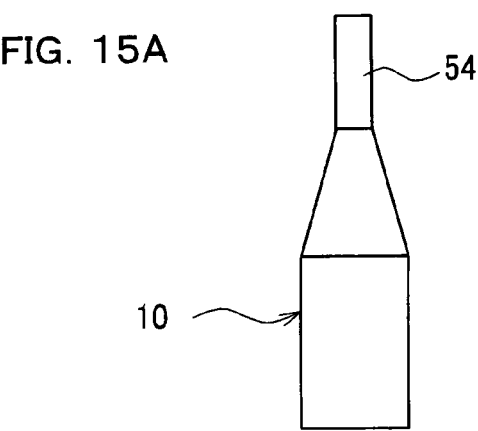
FIG. 15A and FIG. 15B are views each showing a modified example that an extension tube is mounted on a front end of a nozzle of the ultrasonic washer.
Figure 15B:
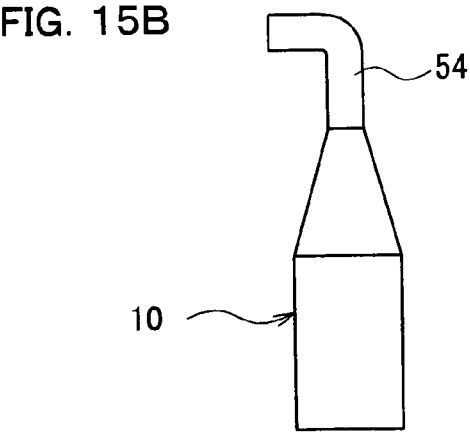

Furthermore, a modified example that an extension tube 54 is mounted on a front end of the nozzle unit 24 of the ultrasonic washer 10 shown in FIG. 4 is shown in FIG. 14. By mounting the extension tube 54 as above, the washing may be splayed more precisely to the portion to be washed. The extension tube 54 may be a straight tube as shown in FIG. 15A, or it may be bent at the tip as shown in FIG. 15B. Furthermore, the extension tube 54 may be detachable for the nozzle unit 24, and it may be formed integrally with the outside member 32 of the nozzle unit 24. In particular, when the extension tube 54 is formed detachable, and when an oral cavity is washed as shown in FIG. 2C, it is possible to wash the deep part of the oral cavity efficiently with using the extension tube 54 of straight tube shown in FIG. 15A, and to wash the back faces of the teeth efficiently with using the extension tube 54 bent at the tip shown in FIG. 15B. Still furthermore, in case of the extension tube 54 bent at the tip shown in FIG. 15B, it is possible to change the direction where the washing is splayed freely by making the extension tube 54 rotatable with respect to the nozzle unit 24, so that the operationality of washing by the user increases.

Figure 16:
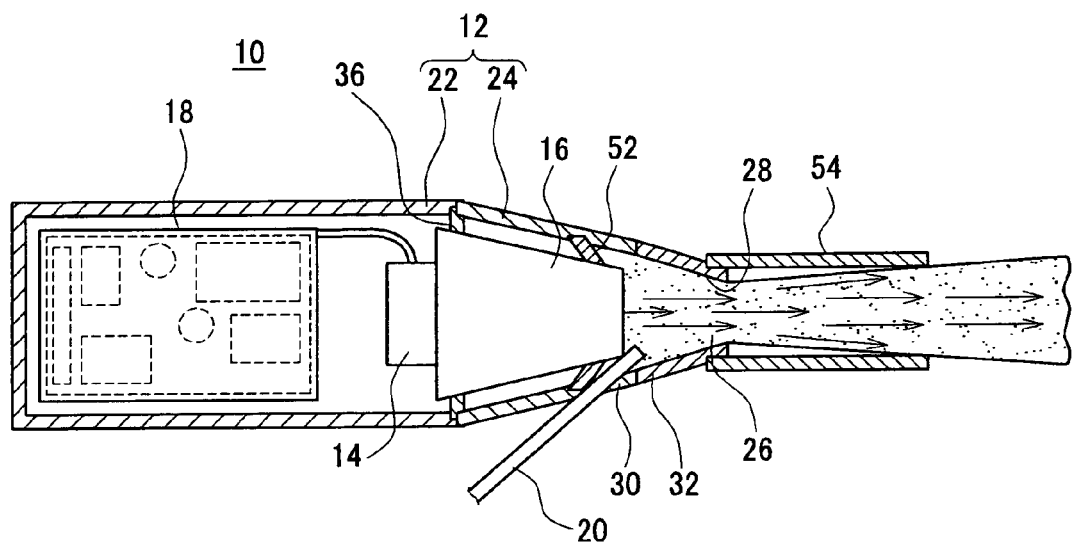
FIG. 16 is a sectional view showing still another constitutional example of the ultrasonic washer in accordance with the second embodiment.
Figure 17:
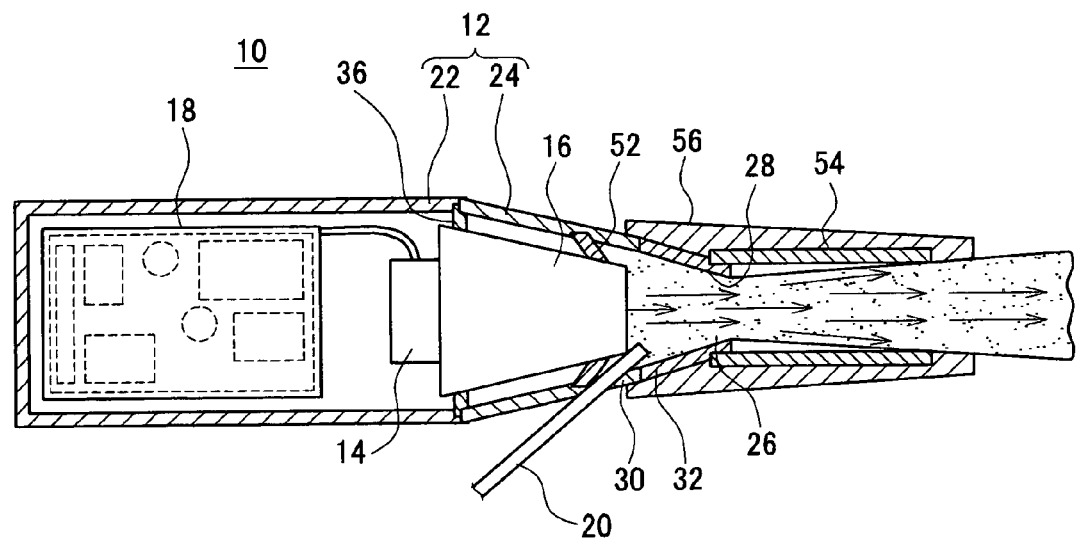
FIG. 17 is a sectional view showing still another constitutional example of the ultrasonic washer in accordance with the second embodiment.

Furthermore, a modified embodiment that the extension tube 54 is mounted on the ultrasonic washer 10 shown in FIG. 13 is shown in FIG. 16. Still furthermore, as shown in FIG. 17, it is possible to mount a protection cover 56 formed of a material having flexibility such as a rubber on an outside of the extension tube 54. Although the extension tube 54 is made of a relatively hard material such as resin or metal, a process such as smoothing the surface thereof or removing sharp edge is generally performed so as not to injure the user. When the user, however, confusedly uses it, the living body such as the gum-ridge in the oral cavity or inside of cheek may be injured. Therefore, the living body can be washed more safely and more comfortably by using the protection cover 56 with such flexibility.

Figure 18A:
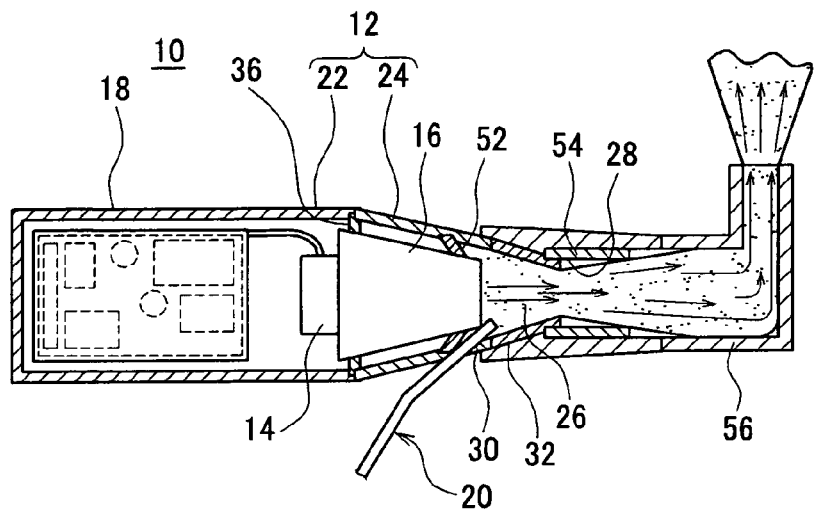
FIG. 18A, FIG. 18B and FIG. 18C are views each showing a modified example that a bent extension tube and a brush are mounted on a front end of a nozzle of the ultrasonic washer.

FIG. 18A shows a modified embodiment that an attachment 58 bent at the tip is further mounted outward of the extension tube 54. It is possible to wash the living body more safely and more comfortably without injuring the living body by using a rubber or the like having flexibility and a certain level of rigidity as a material of the attachment 58.

Figure 18B:
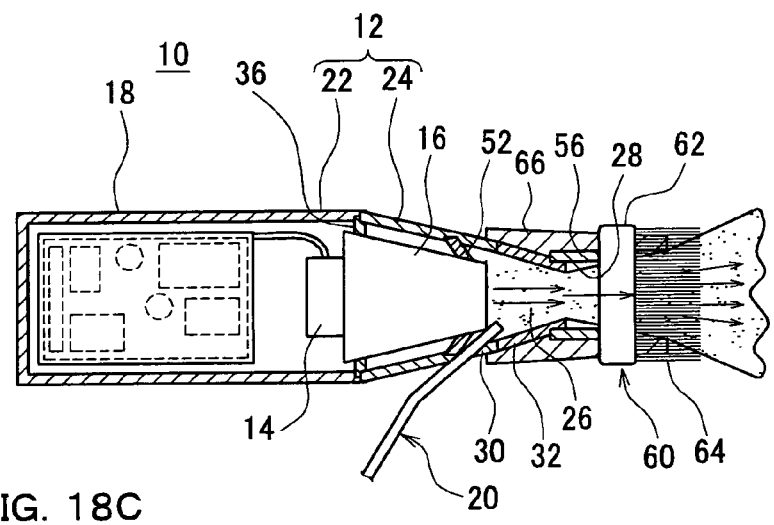
Figure 18C:
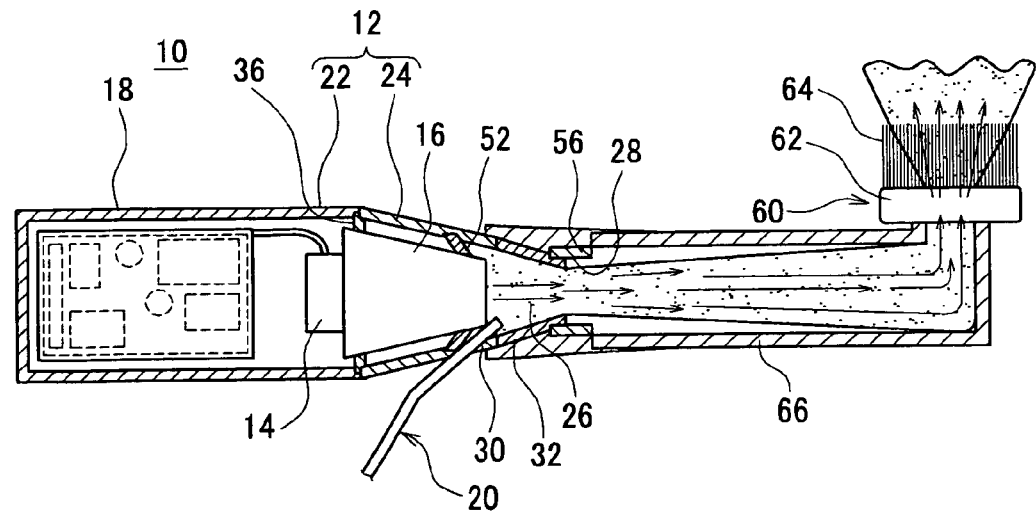

FIG. 18B and FIG. 18C show modified examples that a brush 60 is attached to the extension tube 54 each. The brush 60 is comprised of a base portion 62 on which a lot of holes through which the washing passes are provided, a hair implant 64 transplanted on the base portion, an attaching portion 66, and so on. In FIG. 18C, the attaching portion 66 is extended, and the direction of hair implant of brush 60 is bent in a direction substantially perpendicular to the longitudinal direction of the attaching portion 66. In this way, the washing by the ultrasonic washing can be performed simultaneously with the washing by the brush by attaching the brush 60 on the front end of the nozzle unit 24 of the ultrasonic washer 10.

Figure 19A:
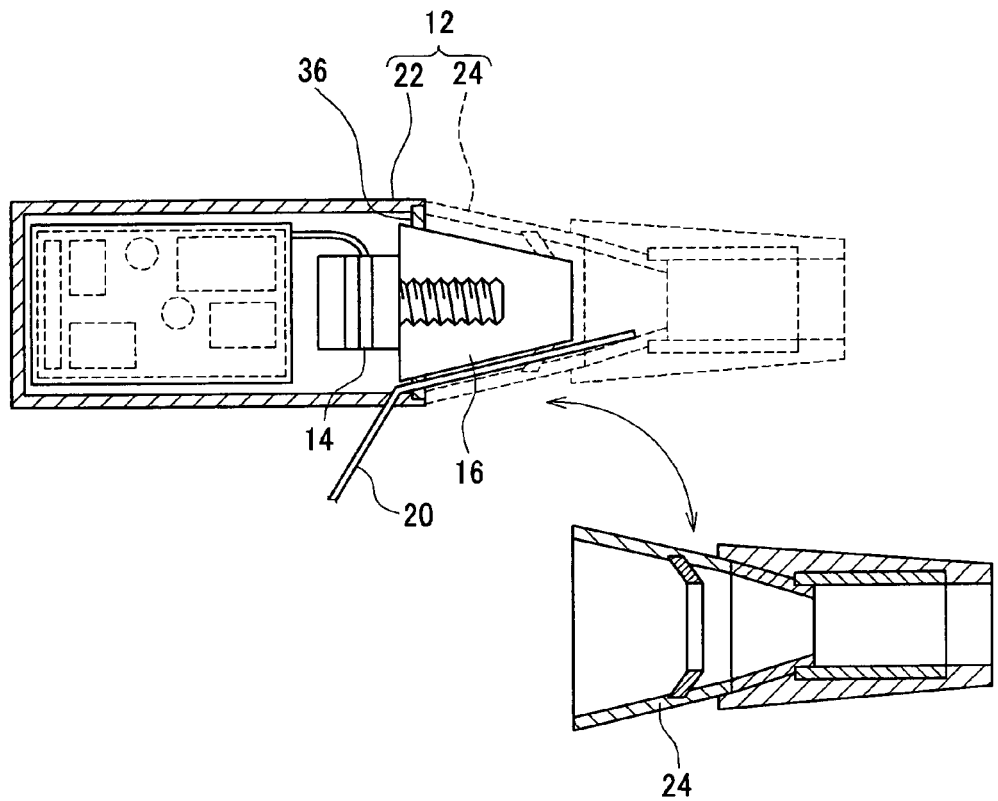
FIG. 19A shows a modified example that a nozzle unit among a housing can be detached from a main body.
Figure 19B:
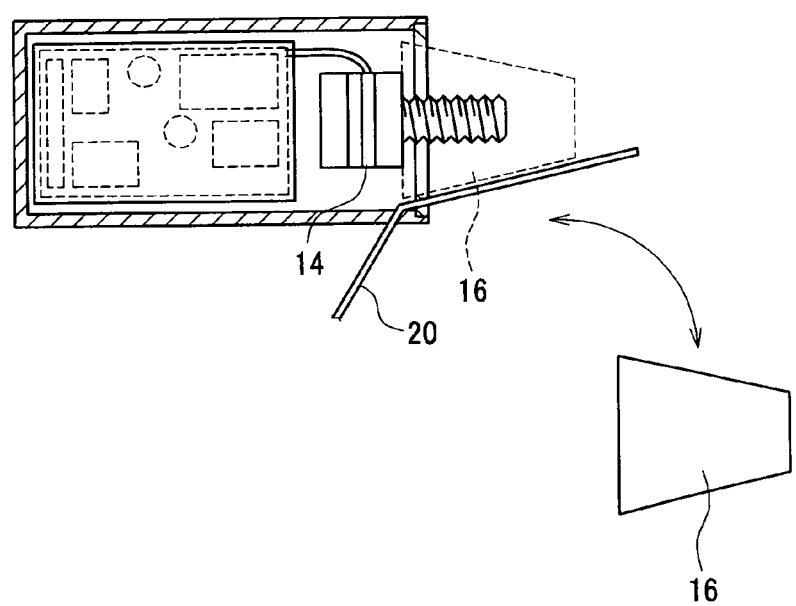
FIG. 19B shows a modified example that the ultrasonic wave propagation member can be separated from the ultrasonic transducer more.

FIG. 19A shows a modified example where the nozzle unit 24 is detachable from the main body 22 in the housing 12. In this way, it is possible to wash the inside of the nozzle unit 24, the outer peripheral portion of the ultrasonic wave propagation member 16, and so on by constituting the nozzle unit 24 detachable. Furthermore, FIG. 19B shows a modified example where the ultrasonic transducer 14 can be separated from the ultrasonic wave propagation member 16. In this way, when the ultrasonic transducer 14 is held in the housing 12 and the ultrasonic wave propagation member 16 is made detachable, it is possible to change the ultrasonic wave propagation member of different shape, for example, shown in FIG. 3 corresponding to the use of the ultrasonic washer 10, characteristics of the object to be washed or the potion to be washed, so that versatility of the ultrasonic washer can be expanded.

Figure 20:
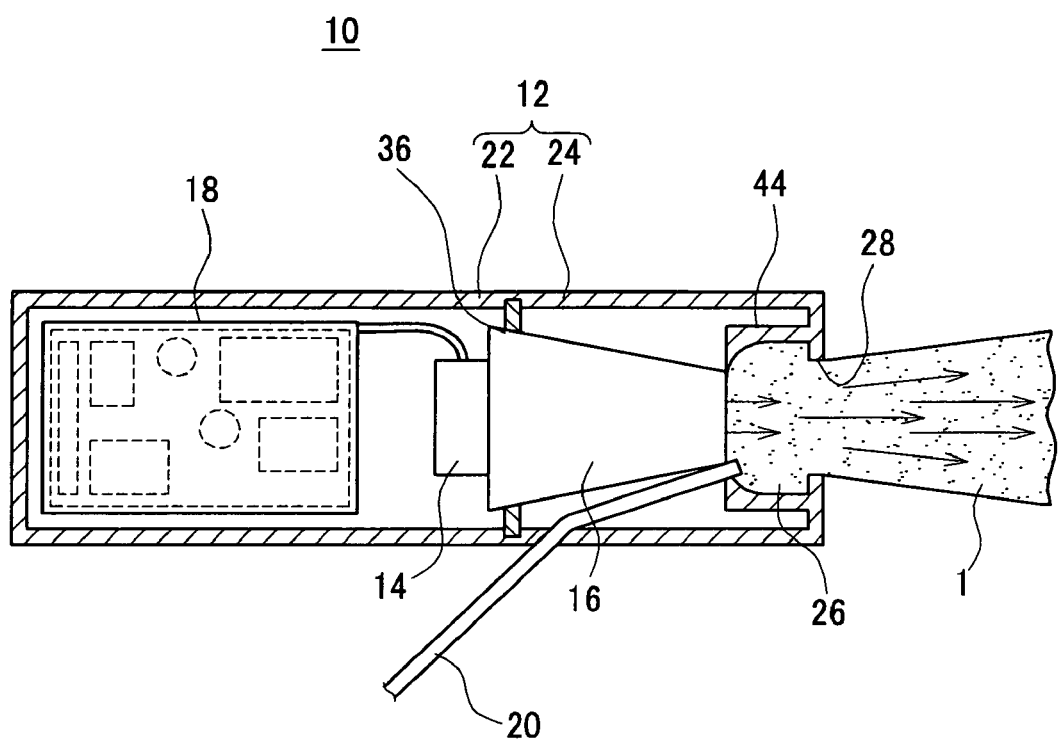
FIG. 20 is a sectional view showing still another constitutional example of the ultrasonic washer in accordance with the second embodiment.

In a modified example shown in FIG. 20, the entire shape of the housing 12 including the nozzle unit 24 is substantially tubular shape, and the ultrasonic wave propagation member 16 and a vessel 44 are provided in the nozzle unit 24 in the ultrasonic washer 10. The ultrasonic wave propagation member 16 is formed substantially frustum so that the cross-sectional area thereof becomes gradually smaller as departing from the ultrasonic transducer 14, and the front end thereof constitutes an inner bottom face of the vessel 44. The water supply pipe 20 is connected to the vessel 44, so that the washing is supplied to the cavity 26. By such a configuration, the effect substantially the same as above can be obtained.

Besides, the modified examples described here can be applied to the ultrasonic washer in accordance with the above-mentioned embodiments and another embodiment described below, and it is needless to say that the same function and effect can be obtained.

Third Embodiment

Subsequently, an ultrasonic washer 10 in accordance with a third embodiment of the present invention is described. In the third embodiment, the ultrasonic washer 10 is constituted as cordless. Besides, with respect to the portions substantially the same as those in the above-mentioned embodiments, description of them is omitted, and only dissimilarity is described.

Figure 21:
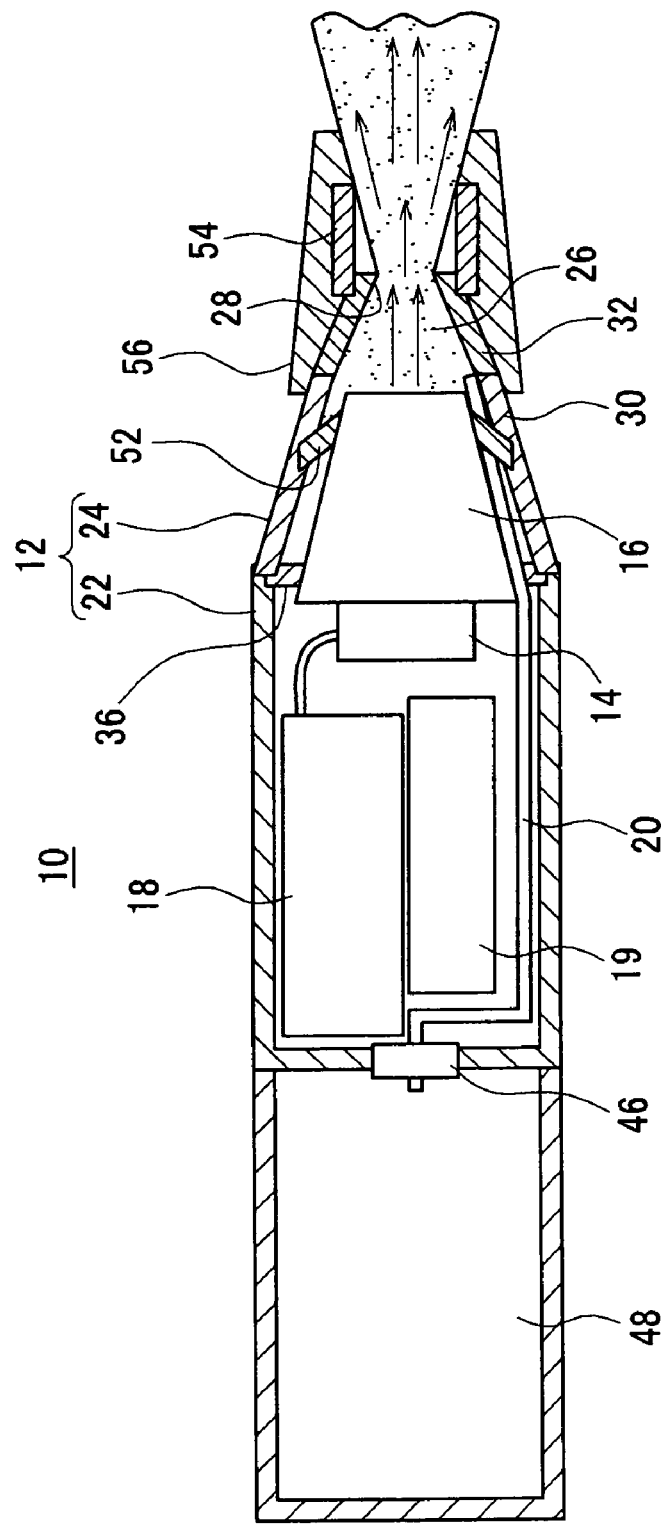
FIG. 21 is a sectional view showing a constitutional example of an ultrasonic washer in accordance with a third embodiment.

In the ultrasonic washer 10 shown in FIG. 21, a rechargeable battery 19 and a pump 46 are provided in an inside of the main body 22 of the housing 12, and a washing tank 48 for pooling the washing is detachably mounted on a rear portion of the main body 22. In this way, when the washing tank 48 is provided on the ultrasonic washer 10 in it and constituted as cordless, it is possible to provide an ultrasonic washer superior to the portability and operationality.

Figure 22:
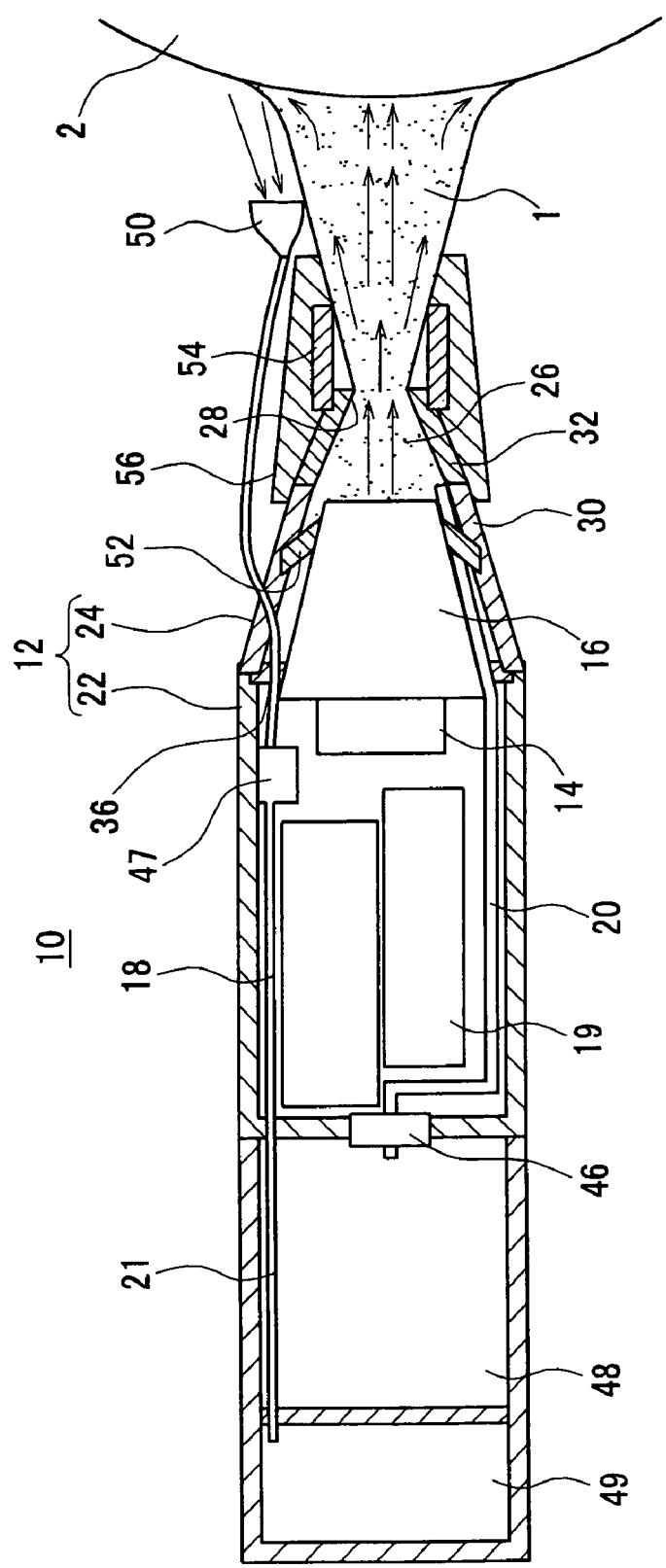
FIG. 22 is a sectional view showing another constitutional example of the ultrasonic washer in accordance with the third embodiment.

FIG. 22 shows a modified example comprising a waste fluid collecting function for collecting the waste washing 1 bounced from the object to be washed or the portion to be washed 2. The ultrasonic washer 10 further comprises an absorption nozzle 50 provided in the vicinity of the front end, a waste fluid absorption pump 47 provided in the inside of the main body 22, an waste fluid tank 49 provided below the washing tank 48, and a water absorption pipe 21 provided from the absorption nozzle 50 to the waste fluid tank 49 through the waste fluid absorption pump 47. In this way, it is possible to reduce a quantity of the washing flying in a circumference of the object to be washed or the portion to be washed 2, and to make the post-treatment after washing easier by having a function to collect a part of the washing splayed to the object to be washed or the portion to be washed 2.

Figure 23:
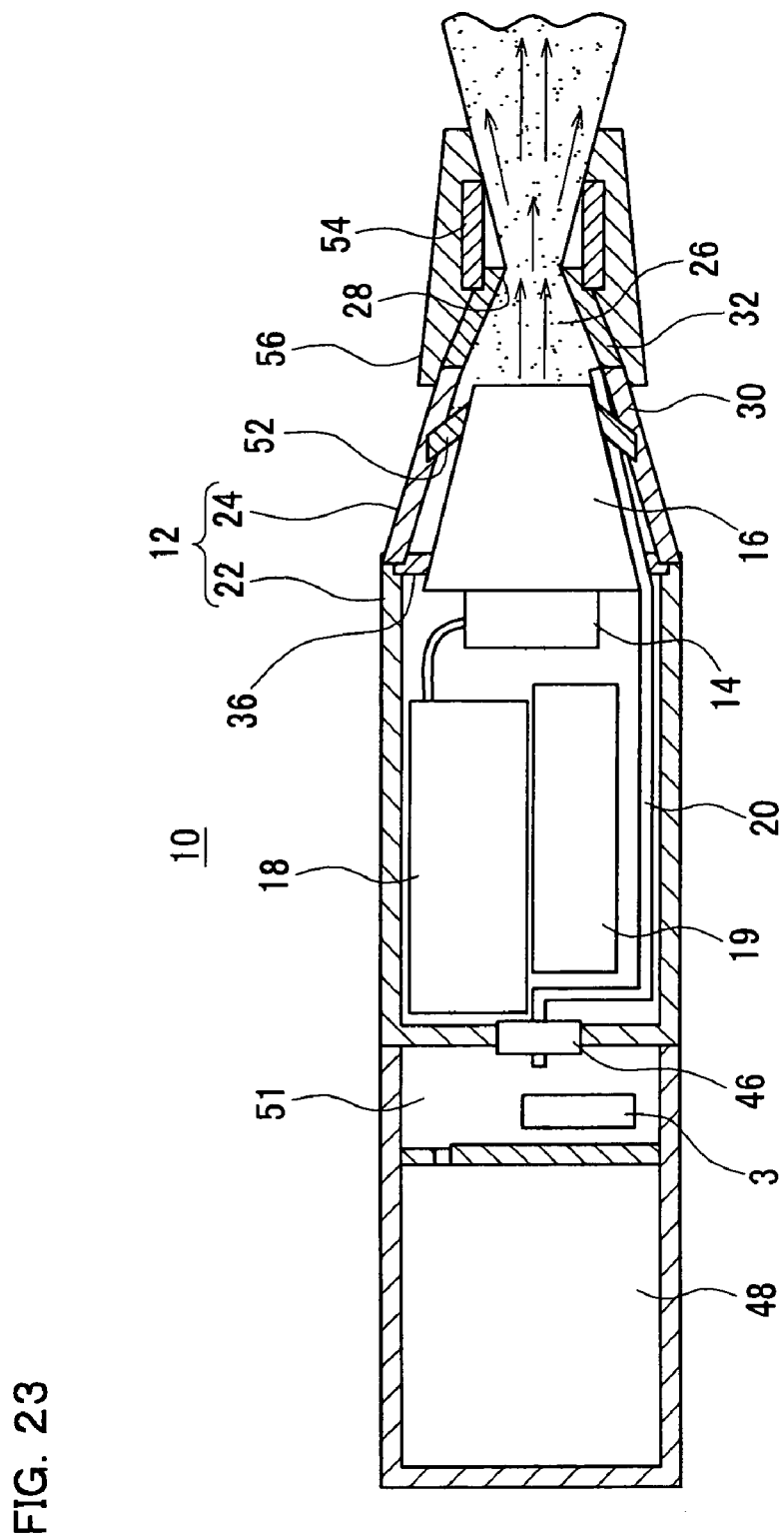
FIG. 23 is a sectional view showing still another constitutional example of the ultrasonic washer in accordance with the third embodiment.

FIG. 23 shows a modified example where a medicament issuance unit 51 is further provided on the washing tank 48. By casting a medicament 3 such as a solid disinfectant or detergent into the medicament issuance unit 51, the medicament 3 is dissolved into the washing when the washing such as water is absorbed from the washing tank 48 and passes through the medicament issuance unit 51, so that the washing including medicament component is splayed toward the object to be washed or the portion to be washed from the ultrasonic washer 10. As a result, washing effect of the object to be washed or the portion to be washed can be increased. Alternatively, sterilization process can be performed to the object to be washed or the portion to be washed simultaneously with the wash. Furthermore, the user refills only the water as the washing without preparing the disinfectant or detergent, so that the handling of the ultrasonic washer 10 becomes easier. Besides, it is needless to say that a portion among the ultrasonic washer 10 which is directly exposed to the washing is made of a material having chemical resistance.

Figure 24:
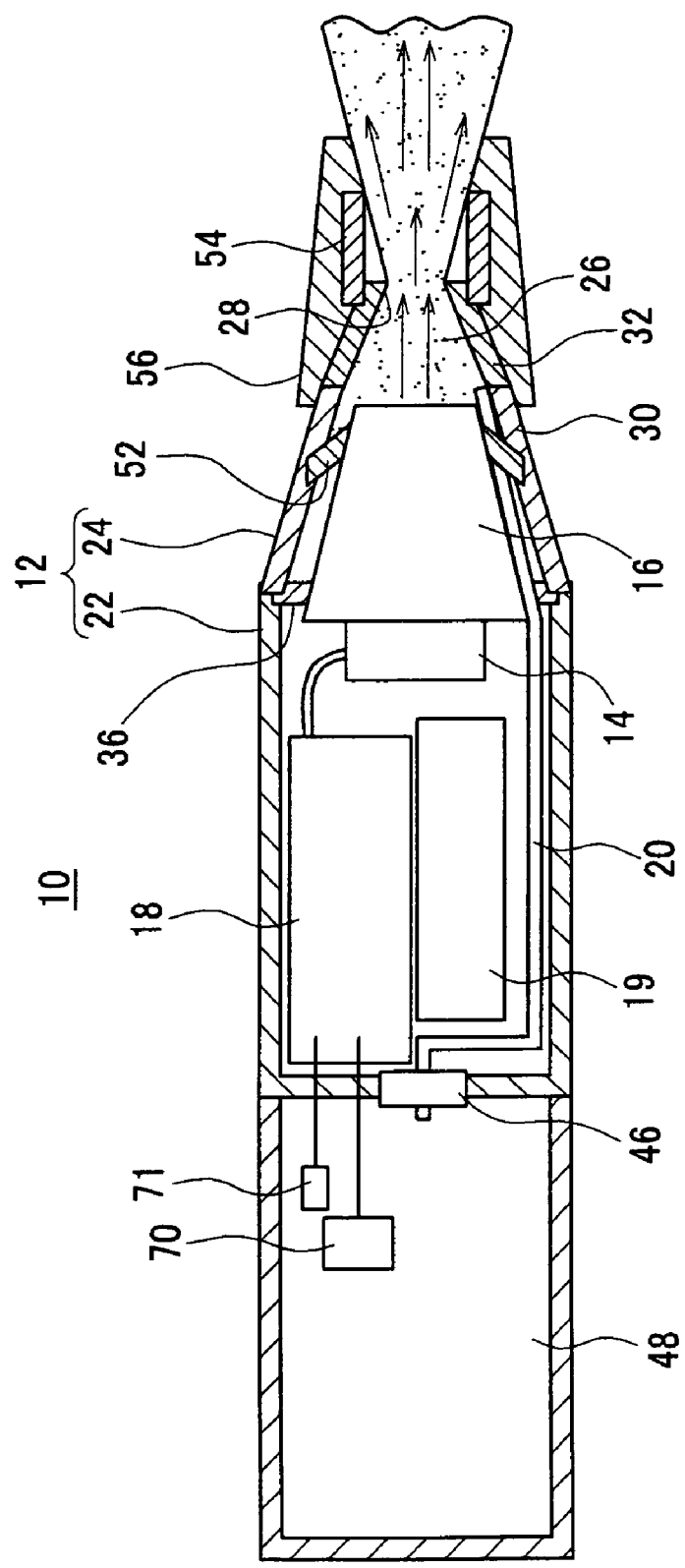
FIG. 24 is a sectional view showing still another constitutional example of the ultrasonic washer in accordance with the third embodiment.

FIG. 24 shows a modified example where a heating conductor 70 and a temperature sensor 71 are provided in the inside of the washing tank 48. For the heating conductor 70, a resistance element or a Peltier element can be used. The driving circuit 18 has a control function of the heating conductor 70, and controls on/off, current value, direction of current for power supply to the heating conductor 70 on the basis of an output signal from the temperature sensor 71 so as to maintain the temperature of the washing in the washing tank 48 in a certain scope. Furthermore, the temperature of the washing to be splayed toward the object to be washed or the portion to be washed from the ultrasonic washer 10, that is, the temperature of the washing in the washing tank 48 can be adjusted optionally depending on the switching operation by the user. Thus, it is possible to wash by the washing of the most suitable temperature corresponding to the characteristics or kind, dirt condition of the object to be washed or the portion to be washed, temperature, or preference or physical condition of the user.

Figure 25:
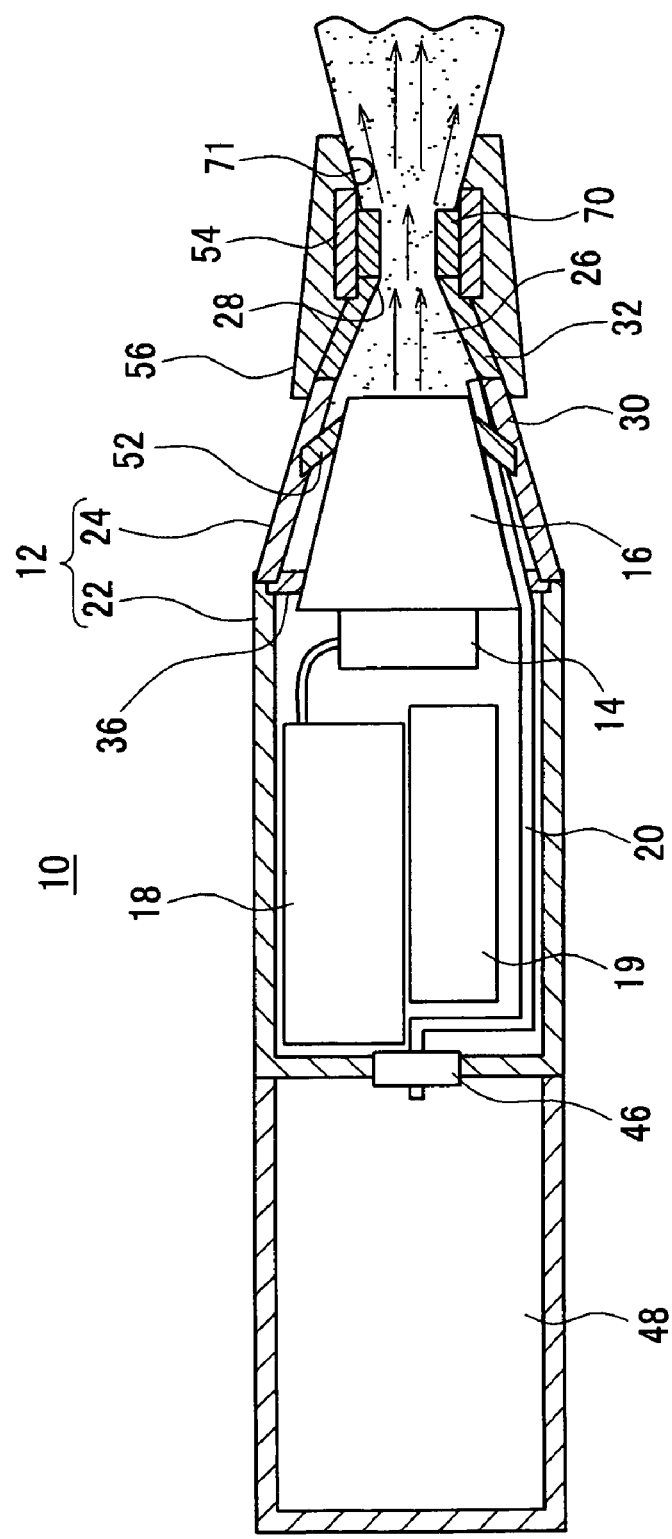
FIG. 25 is a sectional view showing still another constitutional example of the ultrasonic washer in accordance with the third embodiment.

FIG. 25 shows a modified example where the heating conductor 70 and the temperature sensor 71 are provided in the extension tube 54. The function of the driving circuit 18 is similar to the above-mentioned case. Even in a case that no washing tank 48 is provided and the washing is supplied through the water supply pipe 20 from, for example, the faucet of water service, it is possible to heat the washing to a certain temperature and to splay it by applying this modification to the above-mentioned embodiments.

Furthermore, it is possible to heat the washing with utilizing the characteristic of the ultrasonic washer without using the heating conductor 70. Specifically, the washing in the cavity 26 of the nozzle unit 24 is heated with utilizing the character that heating value of the ultrasonic wave propagation member 16 changes by changing the electro-acoustic conversion efficiency of the ultrasonic transducer 14 and the ultrasonic wave propagation member 16. The electro-acoustic conversion efficiency of the ultrasonic transducer 14 and the ultrasonic wave propagation member 16 can be adjusted by changing the LC constant of the driving circuit 18. Furthermore, the heating value of the ultrasonic wave propagation member 16 can be adjusted by changing the oscillation frequency of the ultrasonic transducer 14 within a narrow limit. Still furthermore, the heating value of the ultrasonic wave propagation member 16 can be adjusted by restricting the mechanical oscillation of the ultrasonic wave propagation member 16 with applying mechanical force thereto.

Fourth Embodiment

Subsequently, an ultrasonic washer 10 in accordance with a fourth embodiment of the present invention is described. In the above-mentioned second and third embodiments, the ultrasonic wave propagation member 16 is formed substantially frustum. In the fourth embodiment, the ultrasonic wave propagation member 16, however, is formed another shape. Besides, with respect to the portions substantially the same as those in the above-mentioned embodiments, description of them is omitted, and only dissimilarity is described.

Figure 26A:
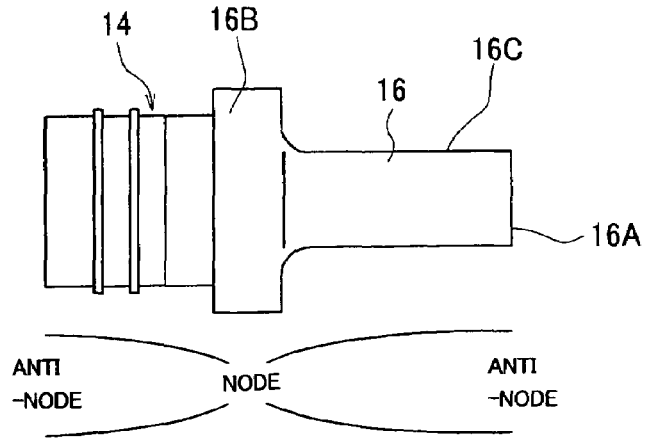
FIG. 26A, FIG. 26B and FIG. 26C are views each showing a configuration of a transducer comprised of an ultrasonic transducer and an ultrasonic wave propagation member used in an ultrasonic washer in accordance with a fourth embodiment of the present invention.

In a constitutional example shown in FIG. 26A, a cross-sectional area of a portion 16B of the ultrasonic wave propagation member 16 of a node of the ultrasonic standing wave oscillation in the vicinity of a side to which the ultrasonic transducer 14 is fixed is made larger and in uniform, and a portion 16C in a side of the ultrasonic wave emission face 16A is formed substantially cylindrical so that a cross-sectional area thereof is made smaller and substantially in uniform.

Figure 26B:
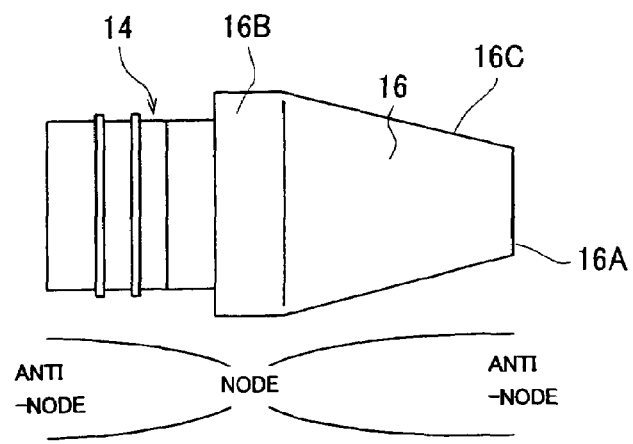

In a constitutional example shown in FIG. 26B, a cross-sectional area of a portion 16B of the ultrasonic wave propagation member 16 of a node of the ultrasonic standing wave oscillation in the vicinity of a side to which the ultrasonic transducer 14 is fixed is made larger and in uniform, and a portion 16C in a side of the ultrasonic wave emission face 16A is formed substantially frustum so that a cross-sectional area thereof becomes gradually smaller.

Figure 26C:
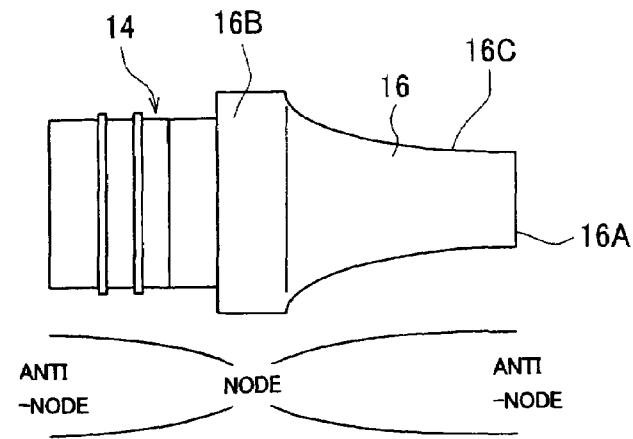

In a constitutional example shown in FIG. 26C, a cross-sectional area of a portion 16B of the ultrasonic wave propagation member 16 of a node of the ultrasonic standing wave oscillation in the vicinity of a side to which the ultrasonic transducer 14 is fixed is made larger and in uniform, and a portion 16C in a side of the ultrasonic wave emission face 16A is formed rotation symmetry having a reflected lateral face of substantially exponential function, hyperbola curve or form of Fourier series so that a cross-sectional area thereof becomes gradually smaller.

Figure 27:
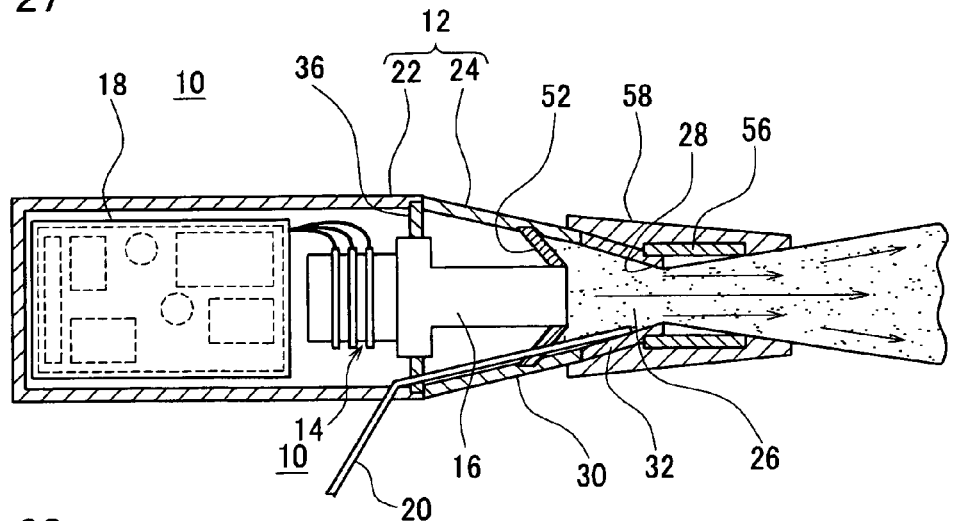
FIG. 27 is a sectional view showing a constitutional example of the ultrasonic washer in accordance with the fourth embodiment.
Figure 28:
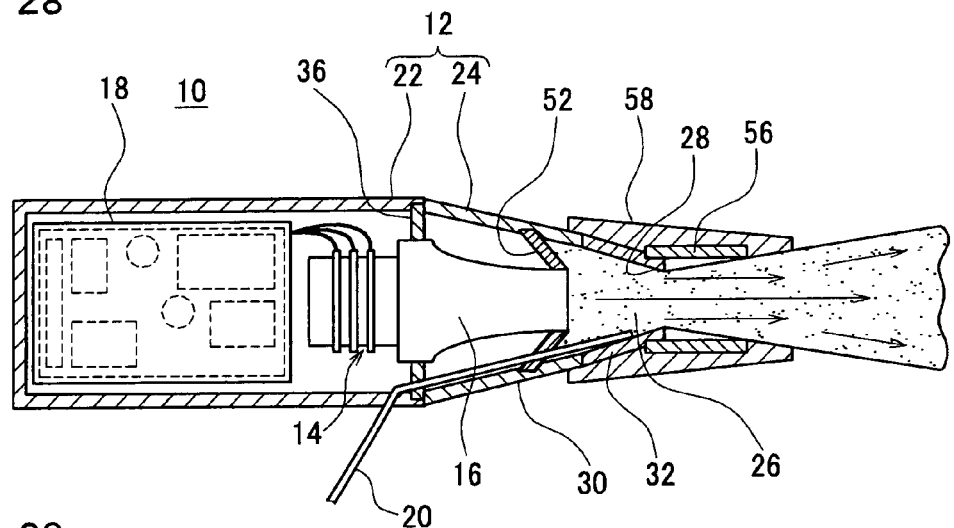
FIG. 28 is a sectional view showing another constitutional example of the ultrasonic washer in accordance with the fourth embodiment.

A configuration of an ultrasonic washer using the ultrasonic wave propagation member 16 shown in FIG. 26A is shown in FIG. 27. Furthermore, a configuration of an ultrasonic washer using the ultrasonic wave propagation member 16 shown in FIG. 26B is shown in FIG. 28. These ultrasonic washers have basically the same configuration of the ultrasonic washer described before except the shapes of the ultrasonic wave propagation member 16, and similar advantageous effect is provided.

Figure 29:
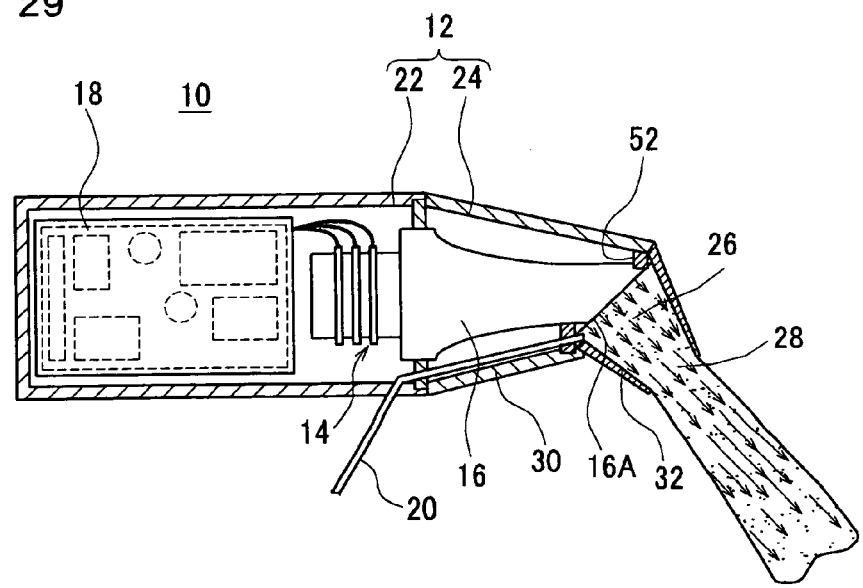
FIG. 29 is a sectional view showing still another constitutional example of the ultrasonic washer in accordance with the fourth embodiment.

FIG. 29 shows an ultrasonic washer using the ultrasonic wave propagation member 16 shown in FIG. 26C. But the ultrasonic wave emission face 16A of the ultrasonic wave propagation member 16 is slanted with respect to the joint face of the ultrasonic transducer 14 and the ultrasonic wave propagation member 16. Furthermore, the outside member of the nozzle unit 24 is mounted to be slanted with respect to the ultrasonic wave emission face 16A of the ultrasonic wave propagation member 16.

Figure 30:
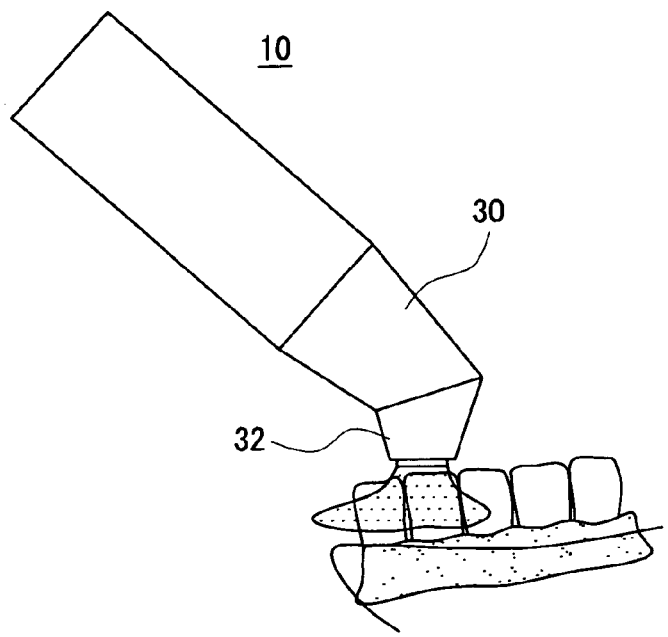
FIG. 30 is a view showing an application example of the ultrasonic washer shown in FIG. 29.

A length among the transducers that is the connection of the ultrasonic transducer 14 and the ultrasonic wave propagation member 16 in a direction perpendicular to the joint face of the ultrasonic transducer 14 and the ultrasonic wave propagation member 16 and passing the center of the ultrasonic wave emission face 16A is set to be an integral multiplication of the half-wavelength in the ultrasonic standing wave oscillation. Furthermore, the transducer that is the connection of the ultrasonic transducer 14 and the ultrasonic wave propagation member 16 is fixed on the housing 12 at a portion of a node in the ultrasonic standing wave oscillation. The ultrasonic vibration generated by the ultrasonic transducer 14 is propagated to the washing in the cavity 26 of the nozzle unit 24 from the ultrasonic wave emission face 16A through the ultrasonic wave propagation member 16, and it is splayed toward the object to be washed or the portion to be washed from the splay opening 28 at the front end of the outside member 32 of the nozzle unit 24. Therefore, for example, as shown in FIG. 30, it is possible to easily wash by splaying the washing toward the portion such as in the oral cavity which is difficult to be washed.

Figure 31:
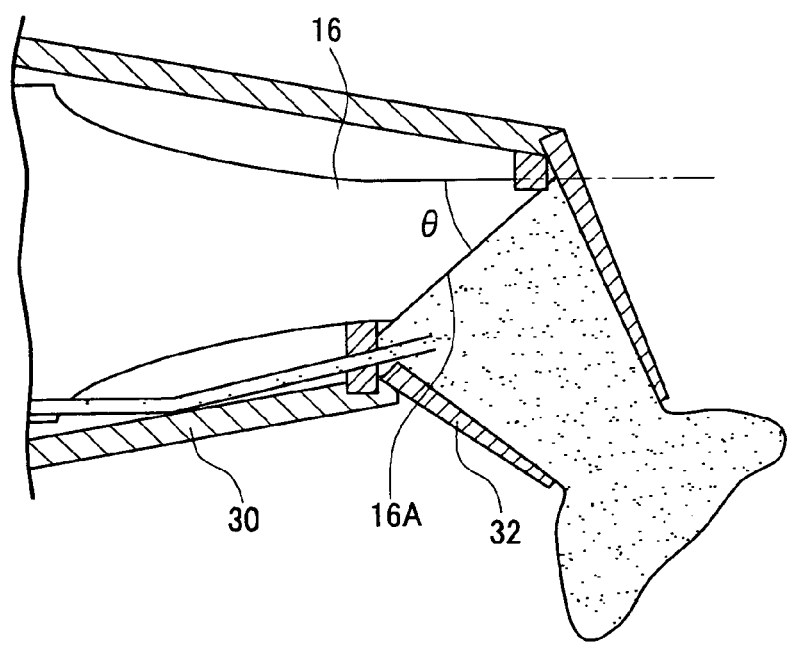
FIG. 31 is a view showing an inclination angle $\theta$ of an ultrasonic wave emitting face of the ultrasonic wave propagation member with respect to a direction perpendicular to a joint face of the ultrasonic transducer and the ultrasonic wave propagation member in the ultrasonic washer shown in FIG. 29.

When an inclination angle of the ultrasonic radiation face 16A with respect to a direction perpendicular to the joint face of the ultrasonic transducer 14 and the ultrasonic wave propagation member 16 is defined as $\theta$ as shown in FIG. 31, an amplitude of ultrasonic wave emitted from the inclined ultrasonic wave emission face 16A becomes $\sin\theta$ times of that of the ultrasonic wave emitted from an ultrasonic wave emission face parallel to a oscillation face of the ultrasonic transducer, so that the amplitude decreases. Therefore, it is preferable to set the inclination angle $\theta$ of the ultrasonic wave emission face 16A equal to or larger than 45 degrees to (less than 90 degrees).

Figure 32:
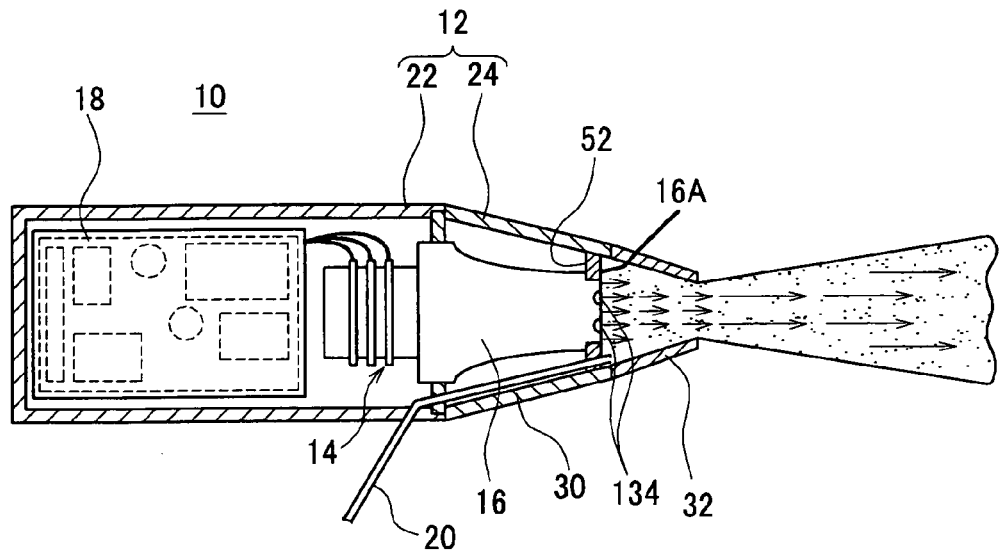
FIG. 32 is a sectional view showing still another constitutional example of the ultrasonic washer in accordance with the fourth embodiment.

FIG. 32 shows a modified example of the ultrasonic washer using the ultrasonic wave propagation member 16 shown in FIG. 26C. Although the ultrasonic wave emission face 16A of the ultrasonic wave propagation member 16 is parallel to the joint face of the ultrasonic transducer 14 and the ultrasonic wave propagation member 16, a plurality of hemispherical concave portions 134 is provided on the ultrasonic wave emission face 16A.

Figure 33:
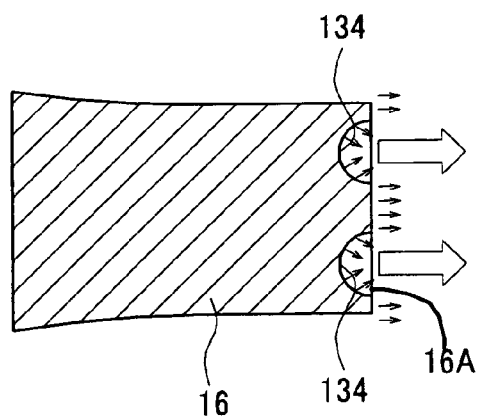
FIG. 33 is a sectional view showing a condition that ultrasonic vibration propagated in the ultrasonic wave propagation member is concentrated to recesses on the ultrasonic wave emitting face in the ultrasonic washer shown in FIG. 32.
Figure 34:
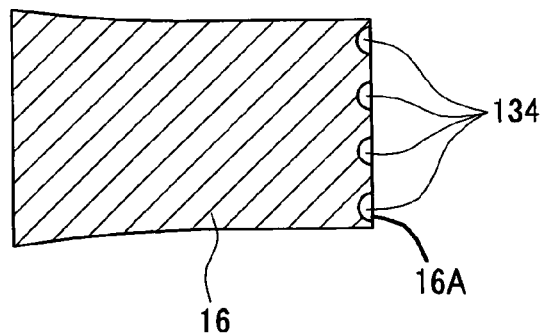
FIG. 34 is a sectional view showing another configuration of the ultrasonic wave propagation member used in the ultrasonic washer shown in FIG. 32.

In this way, when the concave portions 134 are provided on the ultrasonic wave emission face 16A of the ultrasonic wave propagation member 16, the ultrasonic vibration propagating in the inside of the ultrasonic wave propagation member 16 is concentrated to the concave portions of the ultrasonic wave emission face 16A as shown in FIG. 33. Therefore, although a work of the ultrasonic wave propagation member 16 becomes complicated, the ultrasonic wave can be concentrated forward the concave portions 134, and detergency due to the cavitation effect can be increased.

Figure 35:
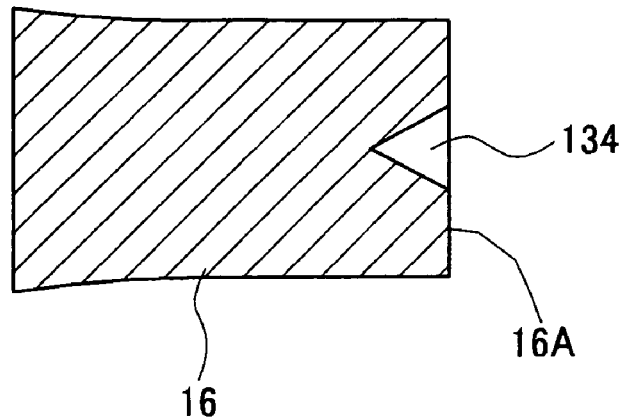
FIG. 35 is a sectional view showing still another configuration of the ultrasonic wave propagation member used in the ultrasonic washer shown in FIG. 32.
Figure 36:
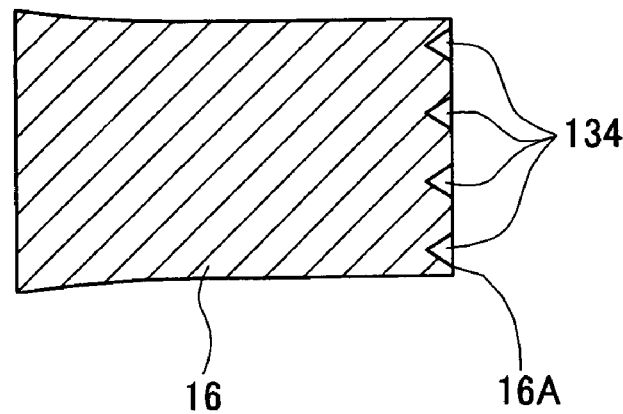
FIG. 36 is a sectional view showing still another configuration of the ultrasonic wave propagation member used in the ultrasonic washer shown in FIG. 32.
Figure 37:
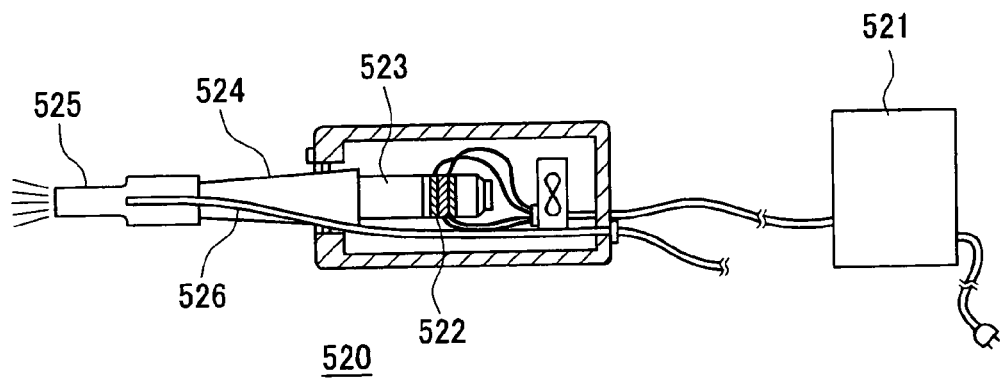
FIG. 37 is a view showing a configuration of a conventional ultrasonic washer.

Besides, it is possible to make the shape of the concave portions 134 smaller and evenly dispersed on the ultrasonic wave emission face 16A. Furthermore, the concave portion 134 is formed to be substantially circular cone shape as shown in FIG. 35 or FIG. 36. Still furthermore, only one concave portion 134 is provided at the center of the ultrasonic wave emission face 16A as shown in FIG. 35. Still furthermore, the shape of the concave portion 134 is not limited to the above hemispherical shape or circular cone shape, and it is sufficient that the shape can concentrate the ultrasonic vibration forward to the concave portion 134. Still furthermore, it is needless to say that the concave portion 134 is provided on the ultrasonic wave emission face 16A of the above each ultrasonic wave propagation member 16.

This application is based on Japanese patent applications 2003-48024 and 2003-342586 filed in Japan, the contents of which are hereby incorporated by references.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

INDUSTRIAL APPLICABILITY

As described above, the ultrasonic washer in accordance with the present invention can be used on hand, so that it is possible to wash a part of living body or articles of daily use easily. Furthermore, since the transmission efficiency of the ultrasonic vibration is higher, enough detergency can be obtained although the output power of the ultrasonic transducer is lowered. Accordingly, it is possible to be driven with a battery, and to make the ultrasonic washer cordless.

The invention claimed is:

1. An ultrasonic washer comprising:
   a housing having a main body and a nozzle unit;
   a water supply pipe for supplying washing to a cavity of said nozzle unit;
   an ultrasonic transducer contained in an inside of the main body of said housing and generating ultrasonic vibration;
   a driving circuit contained in the inside of the main body of said housing and driving said ultrasonic transducer; and
   an ultrasonic wave propagation member provided for protruding into the inside of said main body and into the cavity of said nozzle unit, said ultrasonic transducer being fixed to a portion thereof in said main body side, and directly propagating the ultrasonic vibration generated by the ultrasonic transducer to the washing supplied to the cavity of said nozzle unit from an end face thereof in said nozzle unit side, wherein
   said end face of the ultrasonic wave propagation member in said nozzle unit side is parallel to a joint face of the ultrasonic transducer and the ultrasonic wave propagation member, and a plurality of hemispherical or circular cone shaped concave portions are provided on said end face.

2. The ultrasonic washer described in claim 1, characterized by that said ultrasonic wave propagation member is formed so that a cross-sectional area in a direction parallel to said joint face with said ultrasonic transducer in a vicinity of an end of said nozzle side becomes smaller than an area of the joint face with the ultrasonic transducer.

3. The ultrasonic washer described in claim 2, characterized by that a portion of said ultrasonic wave propagation member protruding into the cavity of said nozzle is formed to be substantially cylindrical shape.

4. The ultrasonic washer described in claim 1, characterized by that a portion of said ultrasonic wave propagation member protruding into the cavity of said nozzle is formed so that across-sectional area in a direction parallel to a joint face with said ultrasonic transducer becomes gradually smaller as approaching to the end portion at said nozzle side.

5. The ultrasonic washer described in claim 4, characterized by that the portion of said ultrasonic wave propagation member protruding into the cavity of said nozzle is formed as one of substantially frustum shape, rotation symmetry having a reflected lateral face of substantially exponential function, hyperbola curve or form of Fourier series.

6. The ultrasonic washer described in claim 1, characterized by that a joint body of said ultrasonic transducer and said ultrasonic wave propagation member performs ultrasonic standing wave oscillation.

7. The ultrasonic washer described in claim 6, characterized by that a length of the joint body of said ultrasonic transducer and said ultrasonic wave propagation member in a direction perpendicular to a joint face of said ultrasonic transducer and said ultrasonic wave propagation member is substantially equal to an integral multiplication of a half-wavelength of the ultrasonic standing wave oscillation.

8. The ultrasonic washer described in claim 7, characterized by that the joint body of said ultrasonic transducer and said ultrasonic wave propagation member is fixed on said housing at a position of a node of said ultrasonic standing wave oscillation.

9. The ultrasonic washer described in claim 1, characterized by that a joint body of said ultrasonic transducer and said ultrasonic wave propagation member constitutes a bolting type Langevin transducer.

10. The ultrasonic washer described in claim 1, characterized by that said ultrasonic transducer generates the ultrasonic vibration by expansion and contraction in thickness direction thereof.

11. The ultrasonic washer described in claim 1, characterized by that said nozzle unit is detachable with respect to said main body.

12. The ultrasonic washer described in claim 1, characterized by that said ultrasonic wave propagation member is detachable with respect to said ultrasonic transducer.

13. The ultrasonic washer described in claim 1, characterized by that a seal member is provided between an inner peripheral face of said nozzle unit and an outer peripheral face of said ultrasonic wave propagation member.

14. The ultrasonic washer described in claim 1, characterized by that said driving circuit adjustably controls at least one of oscillation frequency and output power of ultrasonic wave of said ultrasonic transducer.

15. The ultrasonic washer described in claim 1, characterized by that said driving circuit drives said ultrasonic transducer intermittently, and frequency of intermittent driving is adjustable.

16. The ultrasonic washer described in claim 1, characterized by that said water supply pipe is connected to a washing tank through a pump, and said driving circuit controls driving of said pump.

17. The ultrasonic washer described in claim 16, characterized by that said washing tank is detachable fixed on said main body, and said pump is provided on said main body.

* * * * *